US012042126B2

(12) United States Patent
Araki et al.

(10) Patent No.: US 12,042,126 B2
(45) Date of Patent: Jul. 23, 2024

(54) MONITORING SYSTEM AND EVALUATION METHOD FOR INSERTION OPERATION OF ENDOSCOPE

(71) Applicant: OLYMPUS CORPORATION, Tokyo (JP)

(72) Inventors: Kohei Araki, Hachioji (JP); Kazuma Yamagata, Hino (JP); Hiroaki Kinoshita, Hachioji (JP); Yoshinori Kondo, Hachioji (JP); Takashi Miyazawa, Hino (JP); Harutaka Adachi, Mitaka (JP); Kyoko Nagira, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 446 days.

(21) Appl. No.: 17/502,808

(22) Filed: Oct. 15, 2021

(65) Prior Publication Data

US 2022/0031147 A1 Feb. 3, 2022

Related U.S. Application Data

(63) Continuation of application No. PCT/JP2020/018641, filed on May 8, 2020.

(30) Foreign Application Priority Data

May 30, 2019 (JP) ................. 2019-101321

(51) Int. Cl.
*A61B 1/00* (2006.01)
(52) U.S. Cl.
CPC ........ *A61B 1/0016* (2013.01); *A61B 1/00009* (2013.01); *A61B 1/00071* (2013.01)

(58) Field of Classification Search
CPC .............. A61B 1/0016; A61B 1/00009; A61B 1/00071
See application file for complete search history.

(56) References Cited

U.S. PATENT DOCUMENTS

| 5,558,619 A * | 9/1996 | Kami ................. A61B 1/00042 600/921 |
| 5,840,024 A * | 11/1998 | Taniguchi .............. A61B 5/065 600/424 |
| 6,949,068 B2 * | 9/2005 | Taniguchi ............ A61B 1/0005 600/117 |

(Continued)

FOREIGN PATENT DOCUMENTS

| JP | 2003-180612 A | 7/2003 |
| JP | 2004-348095 A | 12/2004 |

(Continued)

OTHER PUBLICATIONS

International Search Report dated Aug. 4, 2020 received in PCT/JP2020/018641.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

A monitoring system includes an endoscope shape detection apparatus configured to detect a shape of an insertion section of an endoscope and a movement detection apparatus configured to detect a movement of a hand that operates the endoscope.

10 Claims, 16 Drawing Sheets

(56) References Cited

U.S. PATENT DOCUMENTS

| | | | |
|---|---|---|---|
| 7,706,859 B2* | 4/2010 | Aizawa | A61B 5/06 600/117 |
| 8,147,404 B2* | 4/2012 | Miyoshi | A61B 5/06 600/177 |
| 9,125,560 B2* | 9/2015 | Miyoshi | A61B 5/06 |
| 9,448,293 B2* | 9/2016 | Koh | G01R 33/3692 |
| 2004/0193014 A1* | 9/2004 | Miyagi | A61B 1/00042 600/118 |
| 2005/0070757 A1* | 3/2005 | Niwa | A61B 1/00147 600/101 |
| 2014/0167760 A1* | 6/2014 | Koh | G01R 33/3692 324/322 |
| 2017/0347916 A1* | 12/2017 | Hane | A61B 1/00147 |
| 2019/0142256 A1* | 5/2019 | Zhao | A61B 1/00029 600/109 |
| 2022/0031147 A1* | 2/2022 | Araki | A61B 1/00009 |

FOREIGN PATENT DOCUMENTS

| | | |
|---|---|---|
| JP | 2006-288752 A | 10/2006 |
| JP | 4813112 B2 | 11/2011 |
| JP | 2016-538089 A | 12/2016 |
| JP | 2016-539767 A | 12/2016 |
| WO | 2015/070866 A1 | 5/2015 |
| WO | 2017/068650 A1 | 4/2017 |

* cited by examiner

FIG. 11

| TIME POINT | MOVEMENT OF HAND ||||||| INSERTION SECTION || SHAPE INFORMATION | IMAGE INFORMATION |
| | POSITION | POSTURE | TORSION AMOUNT | MOVEMENT AMOUNT | MOVING SPEED | TURNING ANGLE | TURNING SPEED | INSERTION AMOUNT | TURNING AMOUNT | | |
|---|---|---|---|---|---|---|---|---|---|---|---|
| t1 | (x1,y1,z1) | (vx1,vy1,vz1) | r1 | AM1 | SM1 | AR1 | SR1 | L1 | R1 | SH1 | I1 |
| t2 | (x2,y2,z2) | (vx2,vy2,vz2) | r2 | AM2 | SM2 | AR2 | SR2 | L2 | R2 | SH2 | I2 |
| t3 | (x3,y3,z3) | (vx1,vy1,vz1) | r3 | AM3 | SM3 | AR3 | SR3 | L3 | R3 | SH3 | I3 |
| ⋯ | ⋯ | ⋯ | ⋯ | ⋯ | ⋯ | ⋯ | ⋯ | ⋯ | ⋯ | ⋯ | ⋯ |

TBL

MONITORING SYSTEM AND EVALUATION METHOD FOR INSERTION OPERATION OF ENDOSCOPE

CROSS REFERENCE TO RELATED APPLICATION

This application is a continuation application of PCT/JP2020/018641 filed on May 8, 2020 and claims benefit of Japanese Application No, 2019-101321 filed in Japan on May 30, 2019, the entire contents of which are incorporated herein by this reference.

BACKGROUND OF THE INVENTION

1. Field of the Invention

The present invention relates to a monitoring system and an evaluation method for insertion operation of an endoscope.

2. Description of the Related Art

An endoscope has been widely used in a medical field and the like. However, it is not easy to insert an insertion section of the endoscope into a subject. For example, a large intestine has a complicated shape (traveling path). An advanced technique is required for a doctor about operation of the endoscope not to cause pain to a patient when inserting the insertion section of the endoscope into the large intestine.

The doctor can insert the insertion section into the subject while checking a shape of the insertion section inserted into the subject using an endoscope shape acquisition apparatus that displays, in real time, an insertion shape of the insertion section of the endoscope in the subject. However, it cannot be determined only with the insertion shape whether insertion operation of the doctor is good or bad.

International Publication No. 2015/070866 proposes an apparatus for endoscopic examination that presents, about advancing speed, an advancing direction, and a dead time of a selected point in the insertion section, predetermined scores compared with scores of an expert and monitors quality of an endoscopic examination.

SUMMARY OF THE INVENTION

A monitoring system according to an aspect of the present invention includes: a shape detection apparatus configured to detect a shape of an insertion section of an endoscope; and a movement detection apparatus configured to detect a movement of a hand that operates the endoscope.

An evaluation method for insertion operation of an endoscope according to an aspect of the present invention includes: detecting, with a shape detection apparatus, a shape in a subject of an insertion section of the endoscope inserted into the subject; detecting, with a movement detection apparatus, at least one of a position or a posture, in a three-dimensional space, of a hand with which an operator operating the endoscope grips the insertion section; and calculating, with a processor, based on information outputted from the movement detection apparatus and concerning at least one of the position or the posture in the three-dimensional space of the hand, at least one parameter of a movement amount, moving speed, a turning angle, or turning speed of the hand and outputting, temporally in correlation with each other, the at least one parameter and information outputted from the shape detection apparatus and concerning an insertion shape of the insertion section.

BRIEF DESCRIPTION OF THE DRAWINGS

FIG. 11 is a diagram showing an example of a data structure of data for evaluation according to the embodiment of the present invention;

DETAILED DESCRIPTION OF THE PREFERRED EMBODIMENTS

An embodiment of the present invention is explained below with reference to the drawings.

Figure 1:
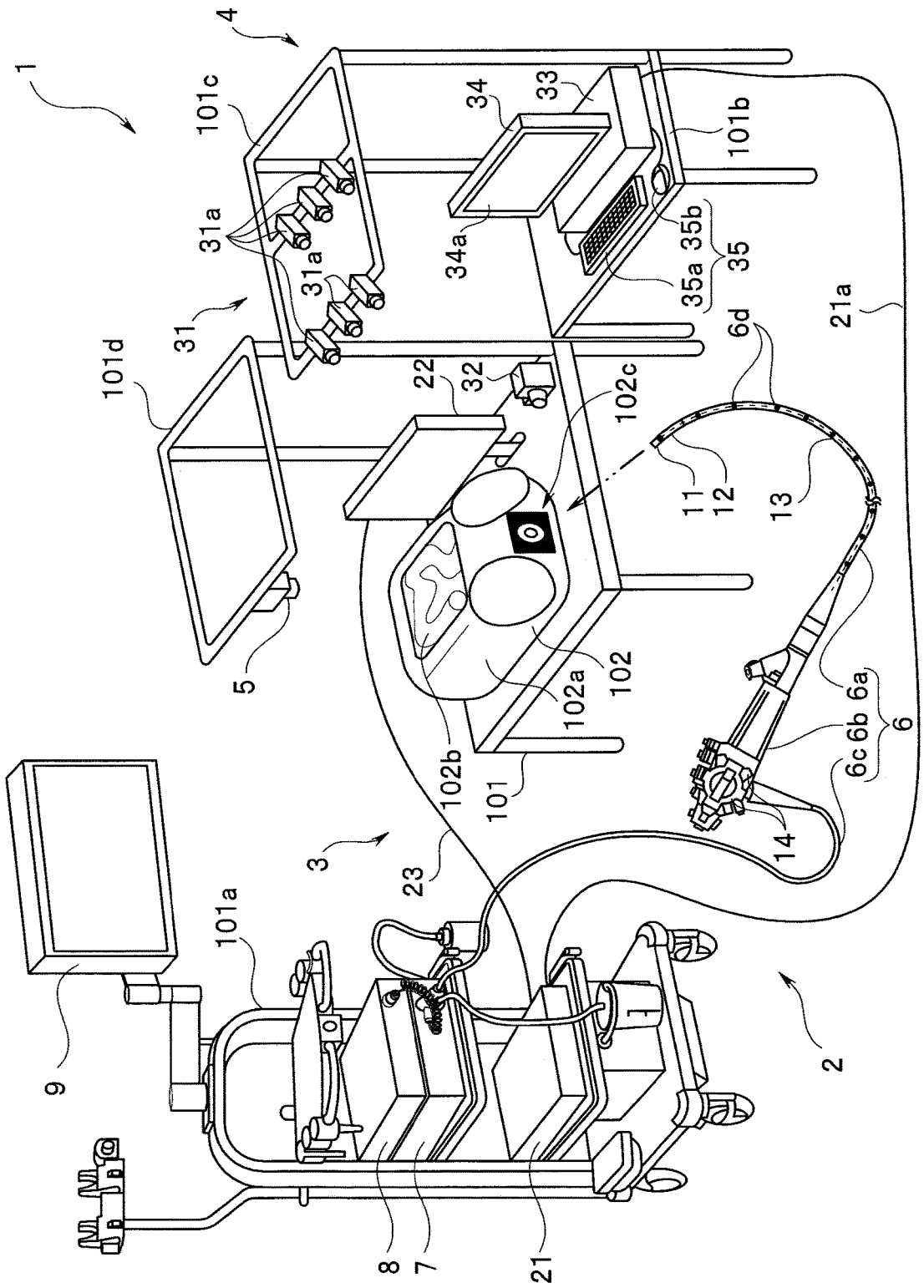
FIG. 1 is a configuration diagram showing a configuration of an endoscope insertion training system according to an embodiment of the present invention.

FIG. 1 is a configuration diagram showing a configuration of a monitoring system according to the present embodiment. The monitoring system mainly includes an endoscope insertion training system (hereinafter simply referred to as training system) 1. The training system 1 includes an endoscope apparatus 2, an endoscope shape acquisition apparatus 3, and an endoscope insertion operation evaluation apparatus 4. The endoscope apparatus 2, the endoscope shape acquisition apparatus 3, and the endoscope insertion operation evaluation apparatus 4 are disposed near a partial model (hereinafter referred to as model) 102 of a human body fixed on a table 101. The model 102 is a colon model. The model 102 includes a main body section 102a simulating a human body shape and includes, in the main body section 102a, an intestinal tract section 102b simulating a large intestine and an anus section 102c simulating an anus. An inside of the intestinal tract section 102b communicates with the anus section 102c.

The endoscope apparatus 2 includes an endoscope 6, an light source apparatus 7, an image processing apparatus 8, and a display apparatus 9. The light source apparatus 7, the image processing apparatus 8, and the display apparatus 9 are placed on a cart 101a or fixed to the cart 101a.

The endoscope 6 includes an insertion section 6a, an operation section 6b, and a universal cord 6c. The insertion section 6a includes a distal end portion 11, a bendable bending section 12, and a flexible tube section 13 in order from a distal end toward a proximal end. The distal end portion 11 is a distal end portion of the insertion section 6a, that is, a distal end portion of the endoscope 6 and is a distal end rigid portion (a distal end configuration portion). An objective optical system and an image pickup device are incorporated in the distal end portion 11. Accordingly, the endoscope 6 includes the insertion section 6a to be inserted into a subject, that is, the model 102.

The bending section 12 includes a plurality of bending pieces and is capable of bending in upward, downward, left, and right directions according to operation on two bending operation knobs 14 of the operation section 6b. The flexible tube section 13 bends according to an external force. The two bending operation knobs 14 are inserted through the insertion section 6a and tow and slack an operation wire in order to bend the bending section 12. The flexible tube section 13 is a tubular member that has flexibility and bends according to an external force.

In the insertion section 6a, a plurality of magnetic sensors 6d for the endoscope shape acquisition apparatus 3 are disposed at a predetermined interval. Note that in the present embodiment, the plurality of magnetic sensors are disposed at an equal interval along a center axis of the insertion section 6a. However, the plurality of magnetic sensors may be disposed at a different interval according to a part where an insertion method is desired to be evaluated. For example, if the part where the insertion method is desired to be evaluated is a sigmoid colon of a large intestine, the number of the plurality of magnetic sensors may be set larger in a distal end side portion of the insertion section 6a than in a proximal end side portion and an interval between the magnetic sensors adjacent to each other may be set narrower in the distal end side portion.

A connector is provided at a distal end of the universal cord 6c. The endoscope 6 is detachably connected to the light source apparatus 7 and the image processing apparatus 8 by the connector. The endoscope 6 is an endoscope insertable into the large intestine. Further, although not shown in FIG. 1, a light guide is inserted through the universal cord 6c. The endoscope 6 is configured to emit, from a distal end of the insertion section 6a through the light guide, illumination light emitted from the light source apparatus 7. Further, a plurality of signal lines for the plurality of magnetic sensors 6d are inserted through the universal cord 6c.

A doctor (hereinafter referred to as user) who desires to evaluate insertion operation of an endoscope uses the training system. The user moves a right hand RH gripping the insertion section 6a in various directions. In a state in which the user grips the insertion section 6a with the right hand RH, the user pushes the insertion section 6a into the large intestine of the model 102 in an axial direction of the insertion section 6a and pulls out the insertion section 6a from the large intestine. Further, in the state in which the user grips the insertion section 6a with the right hand RH, the user turns the insertion section 6a around an axis of the insertion section 6a.

The image processing apparatus 8 receives an image pickup signal transmitted from the image pickup device disposed at the distal end portion 11 of the insertion section 6a, applies predetermined image processing to the image pickup signal, and generates an endoscopic image. The image processing apparatus 8 is connected to the display apparatus 9 by a not-shown signal line. An image signal of the endoscopic image is outputted to the display apparatus 9. The endoscopic image is displayed on a display screen of the display apparatus 9.

The endoscope shape acquisition apparatus 3 includes a shape calculation apparatus 21 and a magnetic field generation apparatus 22. The shape calculation apparatus 21 is placed on the cart 101a. The magnetic field generation apparatus 22 is placed on the table 101. The shape calculation apparatus 21 is connected to the image processing apparatus 8 by a not-shown signal line. The shape calculation apparatus 21 receives, through the image processing apparatus 8, signals of the plurality of magnetic sensors 6d incorporated in the endoscope 6. The shape calculation apparatus 21 is connected to the magnetic field generation apparatus 22 by a signal line 23.

The magnetic field generation apparatus 22 generates a predetermined magnetic field based on a driving signal transmitted from the shape calculation apparatus 21. The respective magnetic sensors 6d detect the magnetic field generated by the magnetic field generation apparatus 22. Detection signals of the magnetic field transmitted from the plurality of magnetic sensors 6d are supplied to the shape calculation apparatus 21. Note that a plurality of magnetic field generation elements may be provided in the insertion section 6a instead of the plurality of magnetic sensors 6d. A magnetic sensor may be provided on an outside of the model 102 instead of the magnetic field generation apparatus 22 to detect positions and postures of the respective magnetic field generation elements.

The shape calculation apparatus 21 calculates a shape of the insertion section 6a in real time based on signals transmitted from the respective magnetic sensors 6d. The shape calculation apparatus 21 is connected to an endoscope insertion operation evaluation processor 33 explained below by a signal line 21a. Information about an insertion shape of the insertion section 6a calculated by the shape calculation apparatus 21 is outputted to the endoscope insertion operation evaluation processor 33. The endoscope insertion operation evaluation processor 33 is capable of generating, based on the received information about the insertion shape, an insertion shape image viewed in a designated visual point direction and displaying the insertion shape image on a display apparatus 34. Accordingly, the shape calculation apparatus 21 configures a shape detection apparatus that detects the insertion shape of the insertion section 6a.

Figure 2:
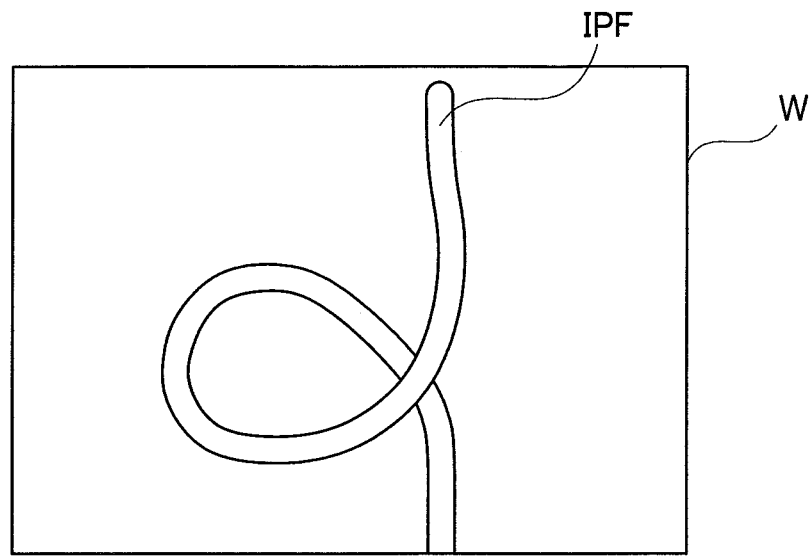
FIG. 2 is a diagram showing an example of an insertion shape image displayed based on insertion shape information from a shape calculation apparatus according to the embodiment of the present invention.

FIG. 2 is a diagram showing an example of an insertion shape image displayed based on insertion shape information outputted from the shape calculation apparatus 21. FIG. 2 shows an insertion shape IPF of the insertion section 6a displayed in one window W on a display screen 34a of the display apparatus 34. However, the insertion shape IPF can also be superimposed on another image and displayed by a software program in the endoscope insertion operation evaluation processor 33.

Referring back to FIG. 1, the endoscope insertion operation evaluation apparatus 4 includes a first image pickup apparatus 31, a second image pickup apparatus 32, the endoscope insertion operation evaluation processor 33, the display apparatus 34, an input apparatus 35, and a bird's eye view camera 36. The input apparatus 35 includes a keyboard 35a and a mouse 35b.

The first image pickup apparatus 31 is fixed to a frame 101c fixed to a table 101b. The second image pickup apparatus 32 is fixed on the table 101. The endoscope insertion operation evaluation processor 33 is placed on the table 101b.

The first image pickup apparatus 31 includes a plurality of cameras 31a. The plurality of cameras 31a pick up, from right and obliquely above of the user, an image of an operation state in which the user operates the insertion section 6a of the endoscope 6 and inserts the insertion section 6a into the model 102. Therefore, the plurality of cameras 31a can pick up an image of the right hand RH of the user.

In the present embodiment, a movement of the right hand RH of the user is detected by infrared-type motion capture. More specifically, a marker apparatus 51 for motion capture is attached to the wrist of the right hand of the user. The respective cameras 31a, which are infrared cameras, pick up images of the marker apparatus 51. A movement of the right hand of the user is detected based on movements of respective markers 54 in the images obtained by picking up the images of the marker apparatus 51 with the respective cameras 31a. A position and a posture of the right hand is detected. In other words, a three-dimensional position and a three-dimensional posture of the marker apparatus 51 are time-sequentially acquired. A behavior of the right hand RH of the user is detected.

Figure 3:
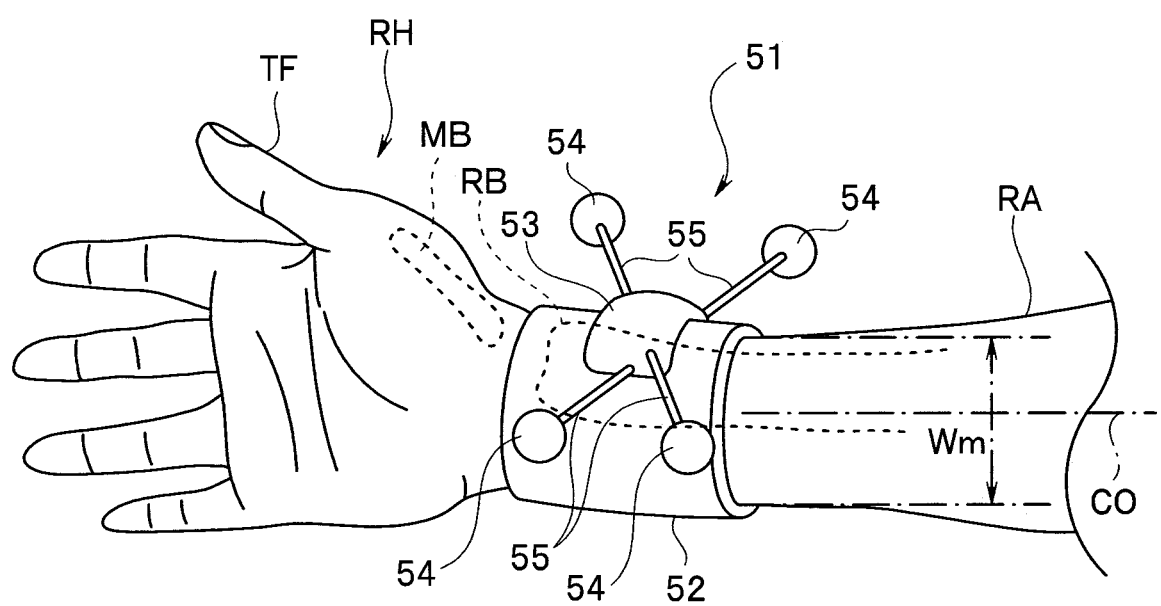
FIG. 3 is a perspective view of a marker apparatus attached to a wrist of a right hand of a user according to the embodiment of the present invention.

FIG. 3 is a perspective view of the marker apparatus 51 attached to the wrist of the right hand RH of the user. The marker apparatus 51 includes a band 52, a main body 53, a plurality of spherical markers 54, and a plurality of shaft members 55. The band 52 has elasticity for attaching and fixing the band 52 to the wrist. The hand 52 is belt-like, includes not-shown fixing means, for example, a hook-and-loop fastener, and is detachably attached to the wrist. The main body 53 is fixed on a surface of the band 52 by an adhesive, a screw, or the like. A plurality of, that is, four shaft members 55 are fixed to the main body 53 to project from the main body 53. In other words, the marker apparatus 51 includes a plurality of markers 54 and is configured to be attached to the wrist of the hand of the user, who is an operator who operates the insertion section 6a.

Figure 4:
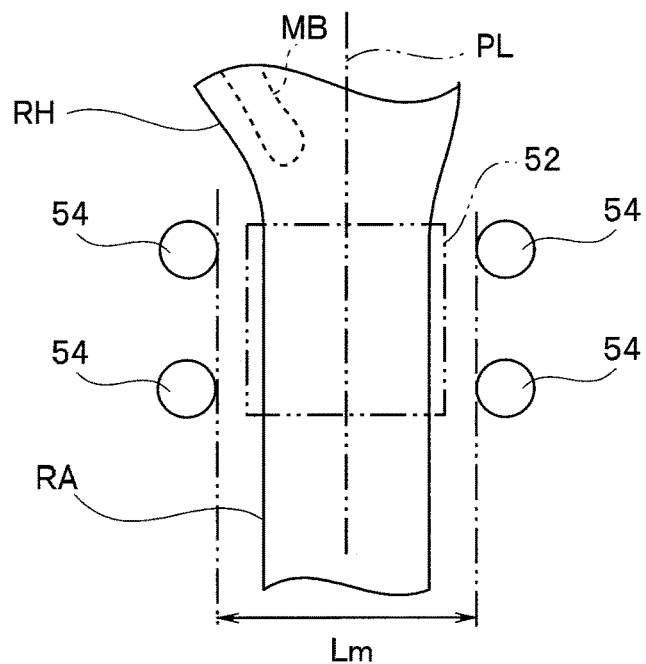
FIG. 4 is a diagram for explaining disposition of four markers at a time when the marker apparatus is attached to the wrist according to the embodiment of the present invention.
Figure 5:
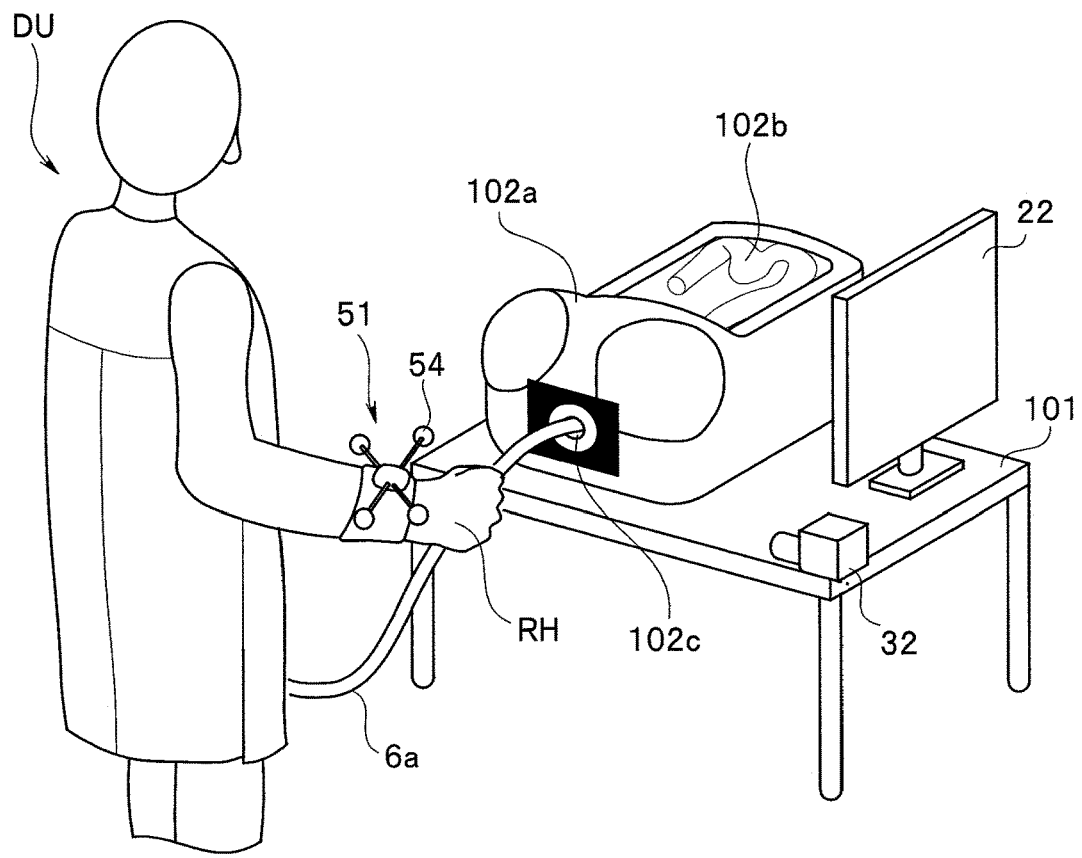
FIG. 5 is a diagram for explaining a state in which a user stands on an anus side of a model and inserts an insertion section into the model according to the embodiment of the present invention.

FIG. 4 is a diagram for explaining disposition of the four markers 54 at a time when the marker apparatus 51 is attached to the wrist. FIG. 5 is a diagram for explaining a state in which a user DU stands on the anus section 102c side of the model 102 and inserts the insertion section 6a into the model 102. As shown in FIG. 5, in a state in which the marker apparatus 51 is attached to the wrist of the right hand RH, the user DU grips the insertion section 6a with the right hand RH and performs push and pull and twisting operation of the insertion section 6a.

In a state in which the user grips the insertion section 6a with the right hand RU, the right hand RH is turned in a range of approximately +90 degrees to approximately −90 degrees around a longitudinal axis CO of a right arm RA. The first image pickup apparatus 31 picks up an image of the right hand RH of the user substantially from above. Accordingly, the marker apparatus 51 is attached to the wrist of the right hand RH such that the main body 53 is located in a position extended from a thumb of the right hand RH toward a radius RB through a first metacarpal MB when viewed in an image pickup direction of the first image pickup apparatus 31.

The respective markers 54 are attached to distal ends of the shaft members 55 extending from the main body 53. In a state in which the marker apparatus 51 is attached to the wrist of the right hand RH, the four markers 54 are located in a direction orthogonal to a plane PL formed by the image pickup direction of the first image pickup apparatus 31 and the longitudinal axis CO of the right arm RA of the right hand RH. The four markers 54 are disposed such that, when the image pickup apparatus 31 is picking up an image of a state in which the wrist of the right hand RH is not turning, a pair of markers 54 are located on both sides of the longitudinal axis CO. The four markers 54 are disposed such that, when an image of the wrist is picked up from the thumb side, two of the four markers 54 are located on one side with respect to the longitudinal axis CO of the right arm RA and the other two markers 54 are located on the other side with respect to the longitudinal axis CO of the right arm RA.

Further, when the right hand RH turns around the longitudinal axis CO of the right arm RA, if the four markers 54 are immediately shadowed by the right arm RA, images of the respective markers 54 cannot be picked up by the image pickup apparatus 31. Therefore, as shown in FIG. 4, a distance Lm between center points of the two markers 54 disposed across the longitudinal axis CO is larger than a maximum outer diameter Wm (FIG. 3) of the right arm RA. The four markers 54 are disposed such that images of at least three of the four markers 54 are picked up by the image pickup apparatus 31 irrespective of how the arm turns. Two or more of combinations of at least two markers 54 among the plurality of markers 54 are disposed to be separated by 80 mm or more to make it possible to detect, with any one of the plurality of cameras 31a, a state in which the plurality of makers 54 project from the wrist. As an example, two or more combinations of the two markers 54 are disposed to be separated by 80 mm or more and 100 mm or less.

The first image pickup apparatus 31 includes the plurality of cameras 31a that pick up images of the plurality of markers 54 in a plurality of directions in a three-dimensional space. The first image pickup apparatus 31 is located above a position of the right hand RH of the user and on a right side or in a front of the user. Six cameras 31a of the image pickup apparatus 31 pick up images of the right hand RH of the user in different directions. The marker apparatus 51 moves according to a movement of the right hand RH. However, the image pickup apparatus 31 is set to pick up an image within a range in which the marker apparatus 51 moves at a normal insertion operation time.

As explained below, by such disposition of the four markers 54, various kinds of operation including insertion operation of the insertion section 6a by the user, more specifically, twisting operation of the right hand RH are detected by picking up images of the various kinds of operation with the image pickup apparatus 31.

The second image pickup apparatus 32 is a camera that picks up an image of a vicinity of the anus section 102c from a side of the model 102. On a surface of the insertion section 6a to be inserted into an anus, characters and figures for detecting an insertion amount are provided by printing or the like. The insertion section 6a is sometimes operated by turning the operation section 6b not only with the right hand RH but also with a left hand. The second image pickup apparatus 32 is provided in order to detect a movement of the insertion section 6a considering a case in which the insertion section 6a is operated using not only the right hand RH but also the left hand. Accordingly, the second image pickup apparatus 32 picks up an image of the insertion section 6a inserted into the model 102, which is a subject.

Figure 6:
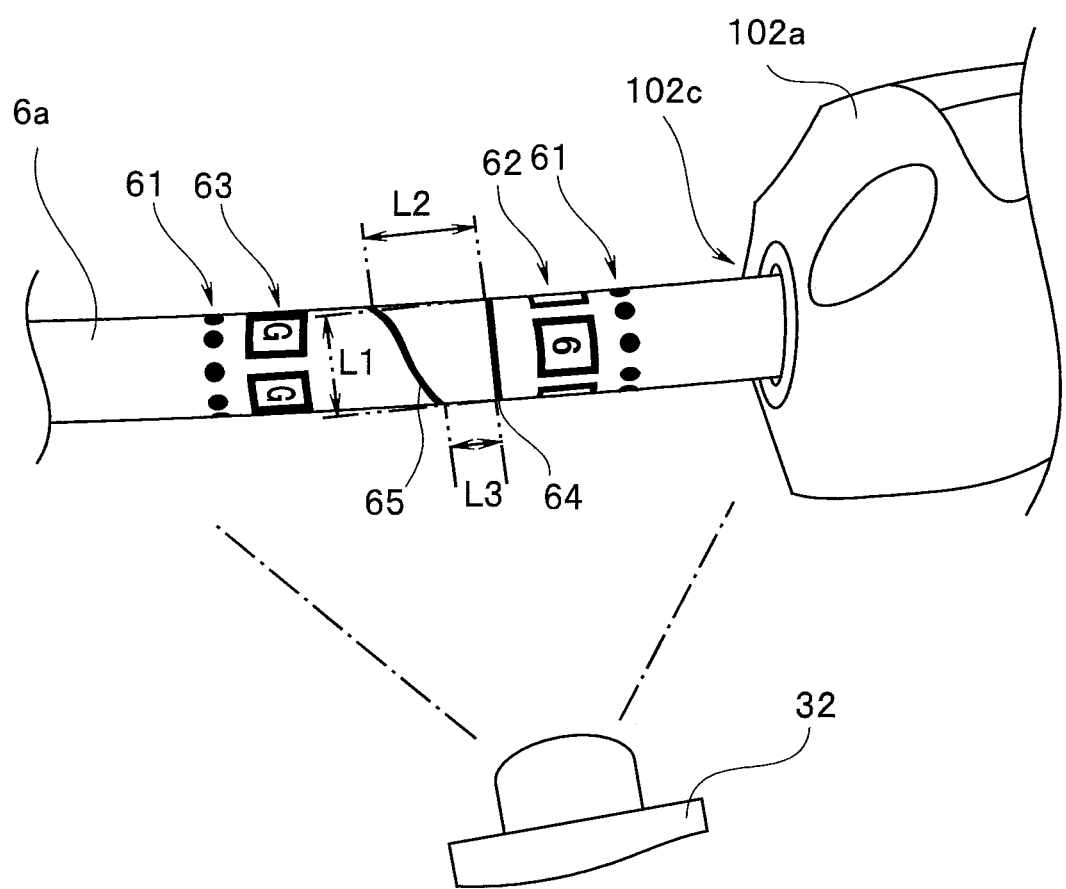
FIG. 6 is a diagram for explaining the insertion section, an image of which is picked up by a second image pickup apparatus, according to the embodiment of the present invention.
Figure 7:
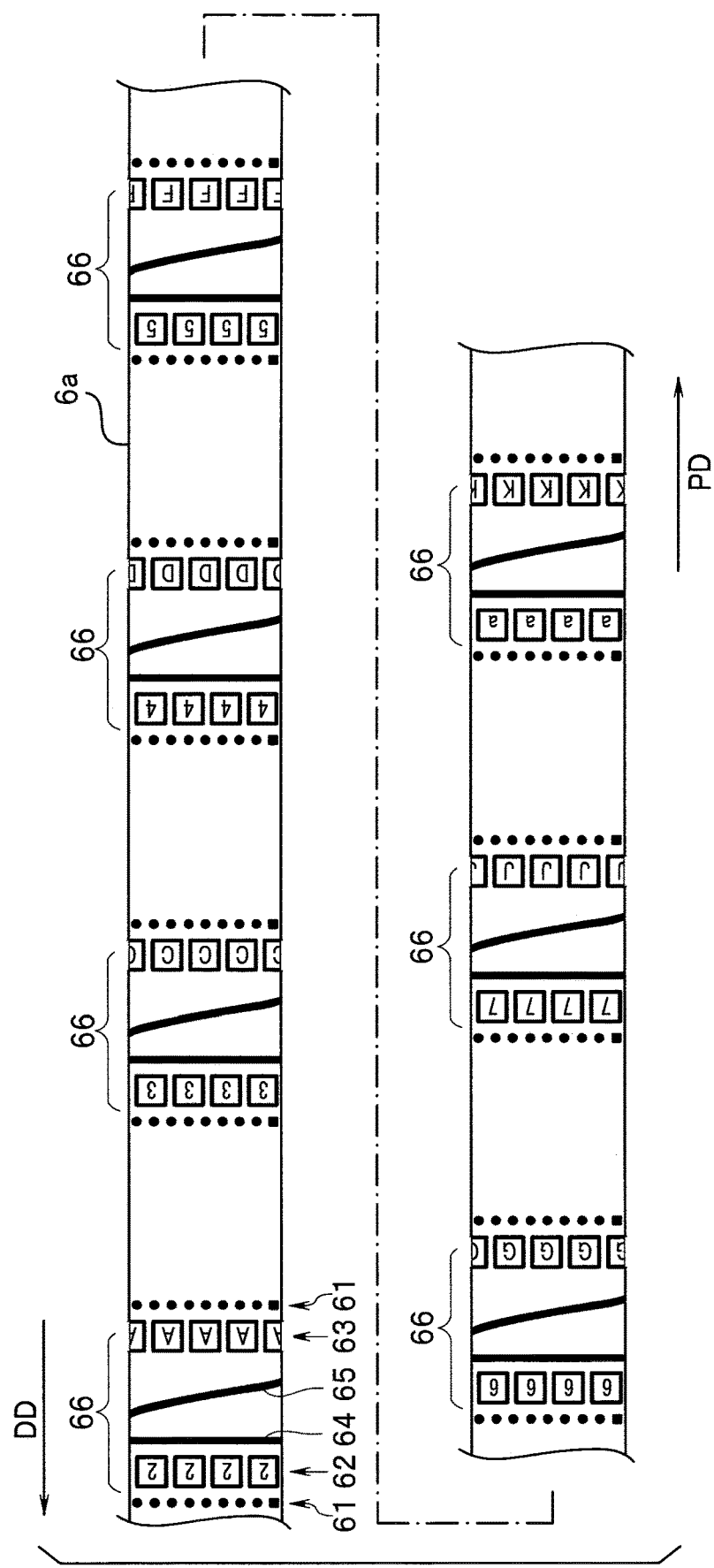
FIG. 7 is a diagram for explaining a plurality of indicators provided on an outer circumferential surface of the insertion section according to the embodiment of the present invention.

FIG. 6 is a diagram for explaining the insertion section 6a, an image of which is picked up by the second image pickup apparatus 32. FIG. 7 is a diagram for explaining a plurality of indicators provided on an outer circumferential surface of the insertion section 6a.

As shown in FIG. 6, the second image pickup apparatus 32 is fixed to the table 101 to be able to pick up an image of the insertion section 6a inserted into the anus section 102c of the model 102. As indicated by an alternate long and short dash line in FIG. 6, the insertion section 6a inserted into the anus section 102c is included in a range in which an image is picked up by the image pickup apparatus 32.

As shown in FIG. 6 and FIG. 7, a plurality of indicators are provided on an outer surface of the insertion section 6a by printing or the like. A plurality of dotted lines 61 provided in a ring shape in a circumferential direction of the insertion section 6a are disposed at a predetermined interval on the outer surface of the insertion section 6a. Further, as one indicator, a first character string 62 is disposed in a ring shape in the circumferential direction of the insertion section 6a. As another indicator, a second character string 63 is also disposed in a ring shape in the circumferential direction of the insertion section 6a.

Characters of the first character string 62 and characters of the second character string 63 are different. The characters of the first character string 62 are numbers or lower-case alphabets and the characters of the second character string 63 are upper-case alphabets. The characters of the first character string 62 and the second character string 63 are printed such that the characters can be correctly read when the insertion section 6a is viewed with a distal end direction DD of the insertion section 6a directed upward and with a proximal end direction PD of the insertion section 6a directed downward. The first character string 62 and the second character string 63 are provided between two dotted lines disposed in the circumferential direction of the insertion section 6a.

As still other indicators, a ring-like line 64 drawing in the circumferential direction of the insertion section 6a and a spiral line 65 on the outer circumferential surface of the insertion section 6a are provided between the first character string 62 and the second character string 63. When viewed in a direction orthogonal to the longitudinal axis of the insertion section 6a, the spiral line 65 is drawn on the outer circumferential surface of the insertion section 6a at 360 degrees around the longitudinal axis to be inclined at a predetermined angle with respect to the longitudinal axis of the insertion section 6a. In other words, a predetermined indicator 66 provided on the outer surface of the insertion section 6a includes the line 64, which is a first band annularly surrounding an outer circumference of the insertion section 6a in the direction orthogonal to the longitudinal axis of the insertion section 6a, and the line 65, which is a second band provided to be tilted with respect to the line 64 and spirally surrounding the outer circumference of the insertion section 6a.

Even if the insertion section 6a turns around the longitudinal axis, a position of the line 64, an image of which is picked up by the image pickup apparatus 32, does not change in the image obtained by the image pickup apparatus 32. On the other hand, when the insertion section 6a turns around the longitudinal axis, a position of the line 65, an image of which is picked up by the image pickup apparatus 32, changes in the image obtained by the image pickup apparatus 32.

Further, as shown in FIG. 7, a plurality of spiral lines 65 are drawn in the same phase. In other words, positions of start points and positions of end points of the spiral lines 65 in a plurality of predetermined indicators 66 are respectively located on imaginary lines on the outer circumferential surface of the insertion section 6a parallel to the longitudinal axis.

The first and second character strings 62 and 63 and the lines 64 and 65 are included in one predetermined indicator 66 and disposed in predetermined positions between two dotted lines 61. The plurality of predetermined indicators 66 are drawn in the insertion section 6a to be separated from one another by a predetermined distance. The predetermined distance is, for example, 10 cm. Accordingly, a distance between two lines 64 adjacent to each other is the same as the predetermined distance. The image pickup apparatus 32 is set such that one predetermined indicator 66 is always included in the range in which an image is picked up by the image pickup apparatus 32.

The first and second character strings 62 and 63 are recognized by character recognition processing in the image obtained by the image pickup apparatus 32. An insertion amount of the insertion section 6a into the large intestine is calculated based on recognized characters and positions of the characters. Note that the two character strings 62 and 63 are used to make it possible to, even if the characters of one of the character strings 62 and 63 are hidden by a hand, read the characters of the other.

As explained below, in the image obtained by the image pickup apparatus 32, a torsion amount, that is, a torsion angle is calculated based on a distance between the two lines 64 and 65 in the respective predetermined indicators 66.

More specifically, the torsion amount is calculated according to a ratio of length L1 of the line 64 and length L2 between the lines 64 and 65 in the image obtained by the image pickup apparatus 32. In FIG. 6, the length L2 is a distance (a longer distance) between an end portion of the line 64 and an end portion of the line 65 of the insertion section 6a. Note that in FIG. 6, as the distance between the end portion of the line 64 and the end portion of the line 65, there are two distances. The distance is a longer distance L2. However, a shorter distance L3 may be used. The torsion amount is calculated according to the ratio of the length L1 of the line 64 and the length L2 between the lines 64 and 65 in order to accurately calculate the torsion amount even if a distance between the insertion section 6a and the image pickup apparatus 32 changes.

The bird's eye view camera 36 is a third image pickup apparatus that is disposed above the model 102 and picks up an image of the intestinal tract section 102b of the model 102. An image pickup signal of the bird's eye view camera 36 is outputted to the endoscope insertion operation evaluation processor 33.

Figure 8:
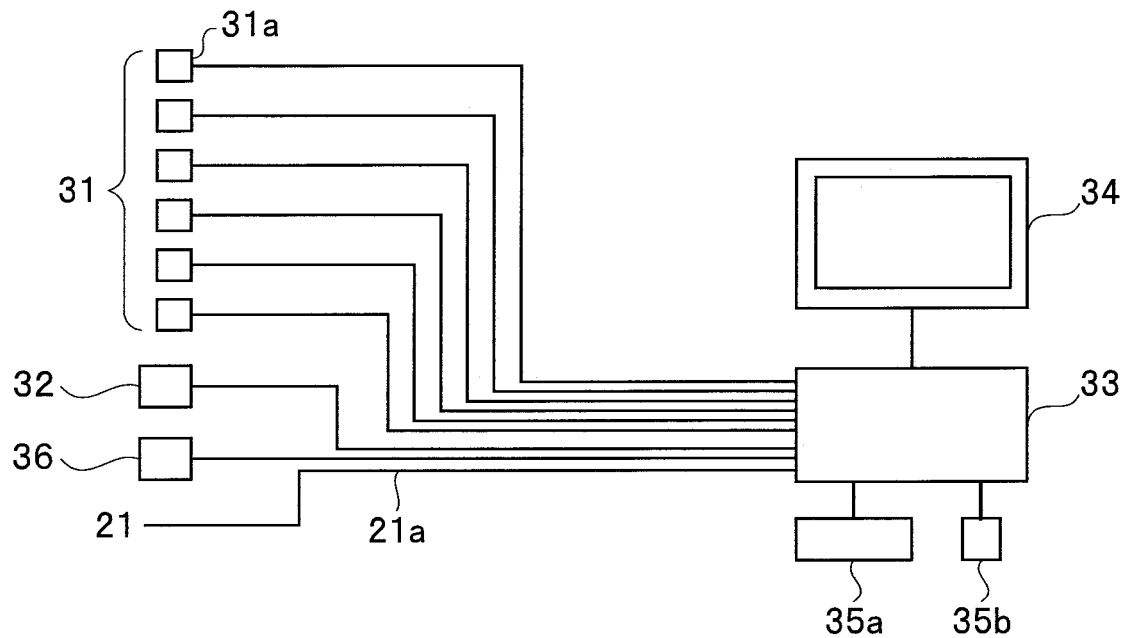
FIG. 8 is a block diagram showing an endoscope insertion operation evaluation apparatus and a plurality of image pickup apparatuses according to the embodiment of the present invention.
Figure 9:
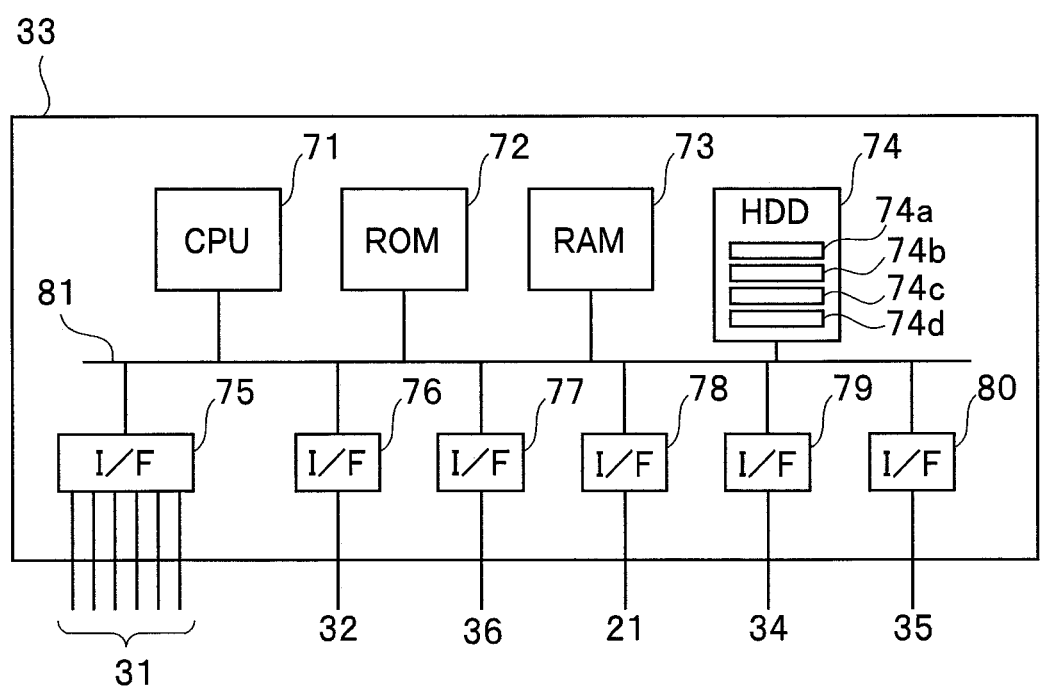
FIG. 9 is a block diagram showing a configuration of the endoscope insertion operation evaluation apparatus according to the embodiment of the present invention.

FIG. 8 is a block diagram showing the endoscope insertion operation evaluation processor 33 and a plurality of image pickup apparatuses. FIG. 9 is a block diagram showing a configuration of the endoscope insertion operation evaluation processor 33.

The endoscope insertion operation evaluation processor 33 is connected to the first image pickup apparatus 31, the second image pickup apparatus 32, the bird's eye view camera 36, which is the third image pickup apparatus that picks up an image of the model 102, and the shape calculation apparatus 21. The endoscope insertion operation evaluation processor 33 performs an arithmetic operation explained below and generates display data on the display apparatus 34.

As shown in FIG. 9, the endoscope insertion operation evaluation processor 33 is a processor including a central processing unit (hereinafter referred to as CPU) 71, a ROM 72, a RAM 73, a hard disk device (hereinafter referred to as HDD) 74, and various interface circuits (hereinafter referred to as I/Fs) 75, 76, 77, 78, 79, and 80. The CPU 71, the ROM 72, the RAM 73, the HDD 74, and the various I/Fs 75, 76, 77, 78, 79, and 80 are connected to one another by a bus 81.

The I/F 75 is an interface between the respective cameras 31a of the first image pickup apparatus 31 and the bus 81. The I/F 76 is an interface between the second image pickup apparatus 32 and the bus 81. The I/F 77 is an interface between the bird's eye view camera 36 and the bus 81. The I/F 78 is an interface between the shape calculation apparatus 21 and the bus 81. The I/F 79 is an interface between the display apparatus 34 and the bus 81. The I/F 80 is an interface between the input apparatus 35 and the bus 81.

The HDD 74 includes a storage region 74a that stores an insertion operation evaluation program EP, a storage region 74b that stores data for evaluation ED, a storage region 74c that stores a motion capture program MC, and a storage region 74d that stores an animation generation program AP. The insertion operation evaluation program EP includes an insertion operation recording program EP1 and an insertion operation display program EP2.

The motion capture program MC is software for detecting positions of the plurality of markers 54 in a plurality of images obtained by the plurality of cameras 31a and calculating a position and a posture, in a three-dimensional space, of the right hand RH to which the marker apparatus 51 is attached. Accordingly, the CPU 71 that executes the motion capture program MC configures a movement detection apparatus that detects a movement including a position and a posture, in a three-dimensional space, of a hand with which the user operating the endoscope 6 grips the insertion section 6a. In particular, the movement detection apparatus is a motion capture apparatus including the first image pickup apparatus 31 that picks up an image of the marker apparatus 51 attached to the hand of the user, the motion capture apparatus detecting a movement of the hand from a movement of the marker apparatus 51, the image of which is picked up by the first image pickup apparatus 31.

The animation generation program AP is software for generating an animation image of a movement of the right hand RH from information of the position and the posture of the right hand RH calculated by the motion capture program MC. Processing of the insertion operation evaluation program EP and a data structure of the data for evaluation ED are explained below.

The CPU 71 can acquire, through the I/F 75, image pickup signals transmitted from the respective cameras 31a. Similarly, the CPU 71 can acquire, through the I/Fs 76 and 77, image pickup signals transmitted from the second image pickup apparatus 32 and the bird's eye view camera 36. The CPU 71 can output generated display data to the display apparatus 34 through the I/F 79.

The CPU 71 reads out the insertion operation evaluation program EP from the HDD 74 and executes the insertion operation evaluation program EP to thereby generate data such as a movement of the hand of the user and records the data for evaluation ED. Further, the CPU 71 can generate display data for evaluation using the data for evaluation ED.

(Action)

Subsequently, the operation of the endoscope insertion operation evaluation processor 33 is explained.

Processing for calculating, recording, and outputting movement information of the right hand RH, shape information of the insertion shape IPF, and movement information and image information of the insertion section 6a in the endoscope insertion operation evaluation processor 33 is performed by the insertion operation evaluation program EP, the motion capture program MC, and the animation generation program AP. The programs are recorded in the ROM 72 or the HDD 74 as explained above. The CPU 71 reads out the programs, develops the programs in the RAM 73, and executes the programs, whereby functions such as detection are realized.

(1) Recording

Figure 10:
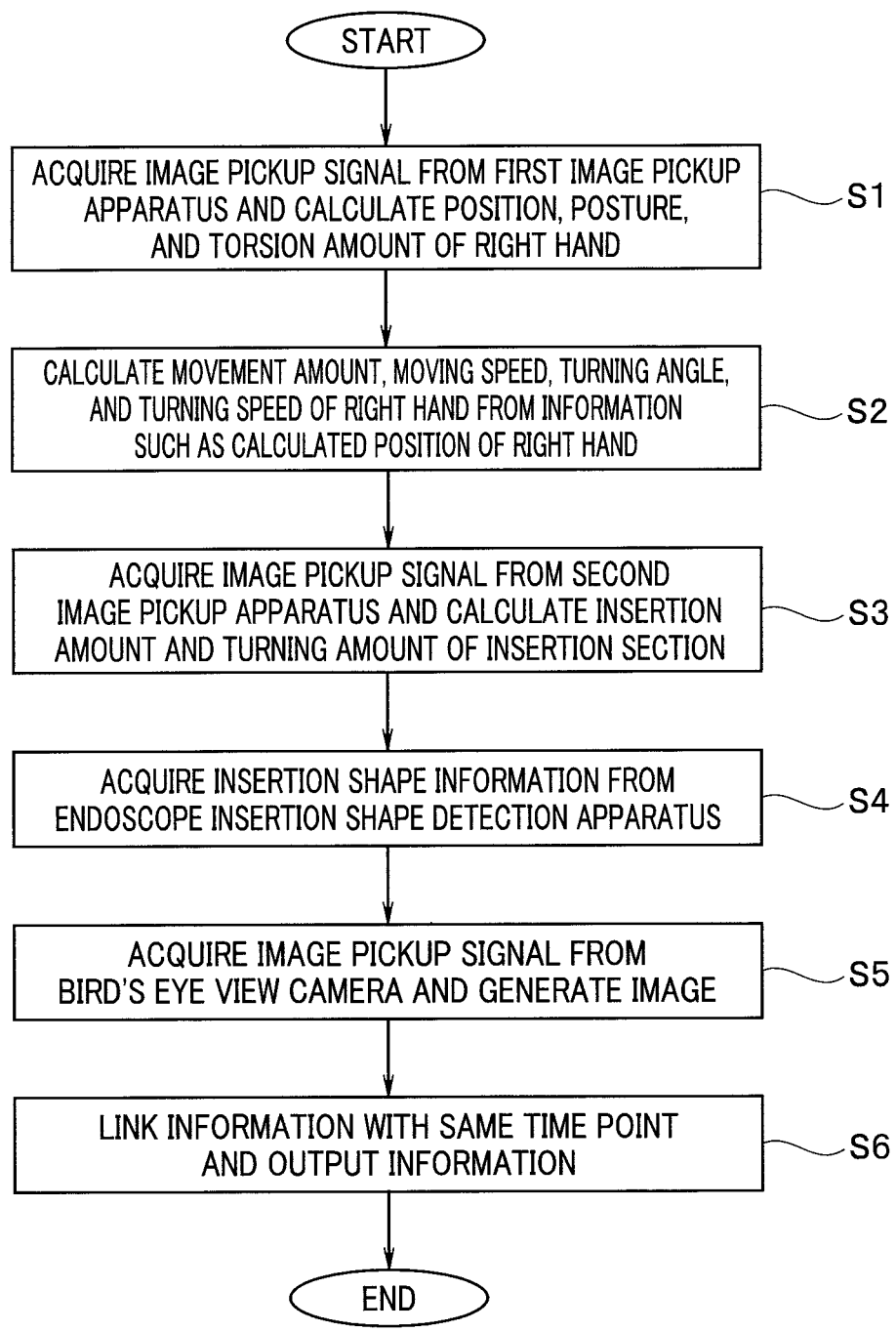
FIG. 10 is a flowchart showing an example of a flow of processing of an insertion method recording program of the endoscope insertion operation evaluation apparatus according to the embodiment of the present invention.

FIG. 10 is a flowchart showing an example of a flow of processing of the insertion operation recording program EP1 of the endoscope insertion operation evaluation processor 33. The CPU 71 reads out the insertion operation recording program EP1 from the FWD 74, develops the insertion operation recording program EP1 in the RAM 73, and executes the insertion operation recording program EP1.

The CPU 71 acquires image pickup signals from the respective cameras 31a of the first image pickup apparatus 31 and calculates a position, a posture, and a torsion amount in the three-dimensional space of the right hand RH (step (hereinafter abbreviated a S) 1). More specifically, the CPU 71 calculates, based on positions in an image of the respective markers 54 of the marker apparatus 51, with the motion capture program MC, a position (x, y, z) and a posture (vx, vy, vz) in the three-dimensional space of the right hand. RH functioning as a rigid body: vx, vy, and vz respectively indicate directions of reference vectors of x, y, and z axes of the right hand RH functioning as the rigid body with respect to x, y, and z axes of the three-dimensional space. The CPU 71 calculates a torsion amount (r) of the right hand RH as well from the calculated position and the calculated posture. The torsion amount (r) is information indicating a turning angle around the longitudinal axis CO of the right arm RA. In this way, the CPU 71 generates information of the position, the posture, and the torsion amount in the three-dimensional space of the right hand RH.

The CPU 71 calculates a movement amount (AM), moving speed (SM), a turning angle (AR), and turning speed (SR) of the right hand RH from the information of the position, the posture, and the torsion amount of the right hand RH calculated in S1 (S2). More specifically, the CPU 71 calculates the movement amount (AM) of the right hand RH in an inserting direction of the insertion section 6a from the information of the position and the posture of the right hand RH calculated in S1. The movement amount (AM) is a push and pull amount of the right hand RH in the inserting direction of the insertion section 6a. The CPU 71 calculates the moving speed (SM) of the right hand RH in the inserting direction of the insertion section 6a from the information of the position and the posture of the right hand RH calculated in S1. The moving speed (SM) is speed of the right hand RH pushing and pulling the insertion section 6a. The CPU 71 calculates the turning angle (AR) of the right hand RH from the information of the torsion amount (r) of the right hand RH calculated in S1. The turning angle (AR) is an angle of the right hand RH functioning as the rigid body around the longitudinal axis of the insertion section 6a. The CPU 71 calculates the turning speed (SR) of the right hand RH from the information of the torsion amount (r) of the right hand RH calculated in S1. The turning speed (SR) is angular velocity of turning of the right hand RH functioning as the rigid body around the longitudinal axis of the insertion section 6a.

The CPU 71 acquires an image pickup signal from the second image pickup apparatus 32 and calculates information of an insertion amount (L) and a turning amount (R) of the insertion section 6a (53). More specifically, the CPU 71 generates an image from the image pickup signal of the image pickup apparatus 32. The CPU 71 calculates the insertion amount (L) and the turning amount (R) of the insertion section 6a from the generated picked-up image and a position and a movement of characters or lines provided on the outer surface of the insertion section 6a.

Accordingly, as explained below, the CPU 71 calculates, based on the picked-up image of the second image pickup apparatus 32, predetermined parameters based on predetermined indicators provided on the outer surface of the insertion section 6a, an image of which is picked up by the second image pickup apparatus 32, and outputs the predetermined parameters temporally in correlation with the information concerning the insertion shape of the insertion section 6a.

The CPU 71 acquires insertion shape information (SH) from the endoscope shape acquisition apparatus 3 (S4). Further, the CPU 71 acquires an image pickup signal from the bird's eye view camera 36 and generates an image (S5). The CPU 71 links the information obtained in S1 to S5 with time point information at the same time point and outputs the information as the data for evaluation ED of the HDD 74 (S6). The data for evaluation ED is recorded in the HDD 74.

The processing in S1 to S6 is repeated at a predetermined period, whereby the data for evaluation is outputted. The respective kinds of information obtained in S1 to S5 are linked with the time point information. In other words, the endoscope insertion operation evaluation processor 33 is configured to calculate parameters of a movement amount, moving speed, a turning angle, and turning speed of the hand based on the information concerning the position and the posture in the three-dimensional space of the hand and output the parameters and the information concerning the insertion shape temporally in correlation with each other.

FIG. 11 is a diagram showing an example of a data structure of the data for evaluation ED. The data for evaluation ED is table data TBL including information such as a position, a posture, and a torsion amount as information concerning a movement of the right hand RH. As explained above, the information of the position (x, y, z), the posture (vx, vy, vz), and the torsion amount (r) of the right hand RH is calculated by the motion capture program MC.

Further, the data for evaluation ED includes information of the insertion amount (L) and the turning amount (R) as information concerning a movement of the insertion section 6a. The insertion amount (L) is information calculated by character recognition of the first character string 62 and the second character string 63 on the outer surface of the insertion section 6a in an image picked up by the image pickup apparatus 32. The turning amount (R) is information calculated based on a distance between the two lines 64 and 65 on the outer surface of the insertion section 6a in the image picked up by the image pickup apparatus 32.

The data for evaluation ED includes the shape information (SH) of the insertion section 6a. The shape information (SH) is information outputted from the shape calculation apparatus 21 and about the insertion shape.

Further, the data for evaluation ED includes the image information (I) of the bird's eye view camera 36. The image information (I) is information of the image generated based on the image pickup signal transmitted from the bird's eye view camera 36.

Note that the data for evaluation ED is one table data TBL shown in FIG. 11. However, the data for evaluation ED may be configured from a plurality of table data.

The data for evaluation ED may not include all of the information shown in FIG. 11 and only has to include at least one piece of information concerning a movement of the hand.

(2) Display

Figure 12:
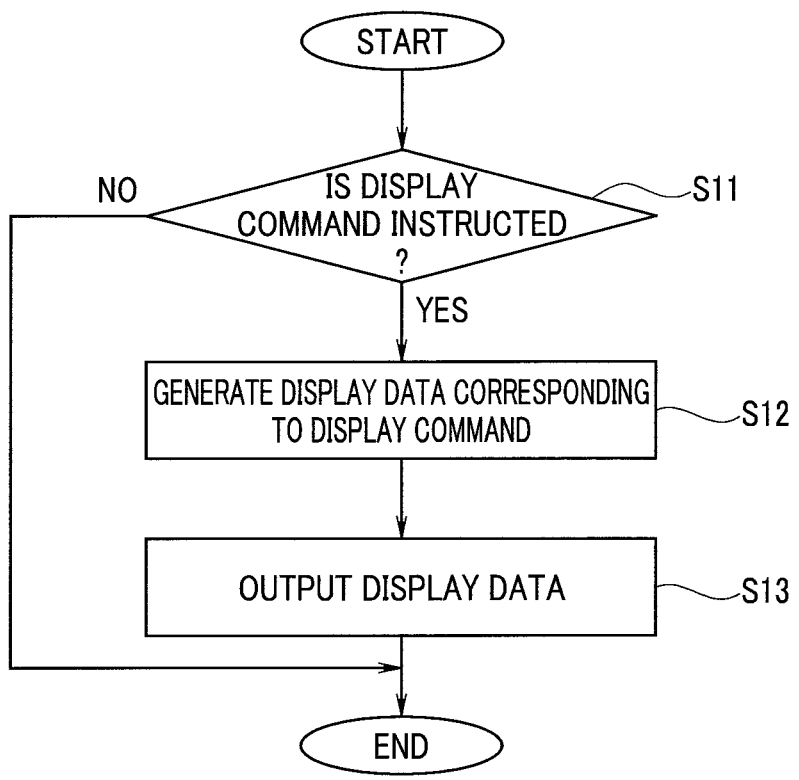
FIG. 12 is a flowchart showing an example of a flow of processing of an insertion method display program of the endoscope insertion operation evaluation apparatus according to the embodiment of the present invention.

FIG. 12 is a flowchart showing an example of a flow of processing of the insertion operation display program EP2 of the endoscope insertion operation evaluation processor 33. The CPU 71 reads out the insertion operation display program EP2 from the HDD 74, develops the insertion operation display program EP2 in the RAM 73, and executes the insertion operation display program EP2. The endoscope insertion operation evaluation processor 33 is capable of generating a plurality of display screens for evaluating insertion operation. The user can operate the input apparatus 35 and give a desired display command to the CPU 71. The CPU 71 performs processing corresponding to the received display command.

The CPU 71 determines whether the display command is instructed from the input apparatus 35 by the user (S11). When the display command is not instructed (S11: NO), the CPU 71 performs no processing. When the display command is instructed (S11: YES), the CPU 71 generates display data corresponding to the display command (S12). The CPU 71 outputs the generated display data to the display apparatus 34 (S13).

Subsequently, an example of display data to be generated is explained.

1) Operation Range of a Hand

For example, the user sometimes desires to compare an operation range of the right hand at a time when the user inserts the insertion section 6a into the large intestine with operation ranges of other users. In that case, when the user inputs a predetermined command, an image shown in FIG. 13 is displayed on the display apparatus 34.

Figure 13:
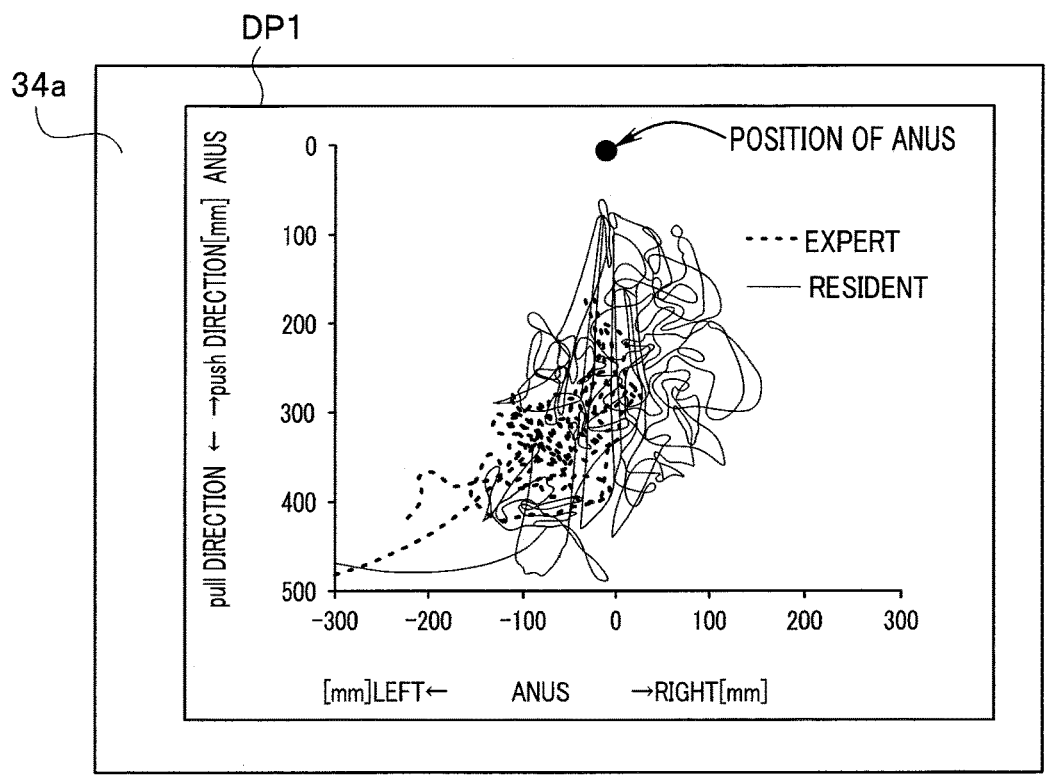
FIG. 13 is a diagram showing an example of an image showing operation ranges of right hands of designated two doctors according to the embodiment of the present invention.

FIG. 13 is a diagram showing an example of an image showing operation ranges of the right hand RH of the user and a designated another user. When the user desires to view a graph in which changes of positions of the right hands RH of the two doctors to be compared are plotted, the user specifies the data for evaluation ED of the two doctors and inputs the predetermined command. Then, a window DP1 in the display screen 34a shown in FIG. 13 is displayed. FIG. 13 is a display example at a time when a user who is a resident, and an expert are selected as the two doctors.

The window DP1 displays a graph showing a change of a position of the right hand RH at a time when the right hand RH of the user is viewed from above. A solid line indicates a trajectory of the right hand RH of the user, who is the resident. A dotted line indicates a trajectory of the right hand RH of the expert. Accordingly, trajectories of positions of the right hands RH from an insertion start to removal in insertion operation by the two doctors are indicated by the solid line and the dotted line. It is seen that a movement of the right hand RH of the resident is more wasteful compared with a movement of the right hand RH of the expert.

Figure 14:
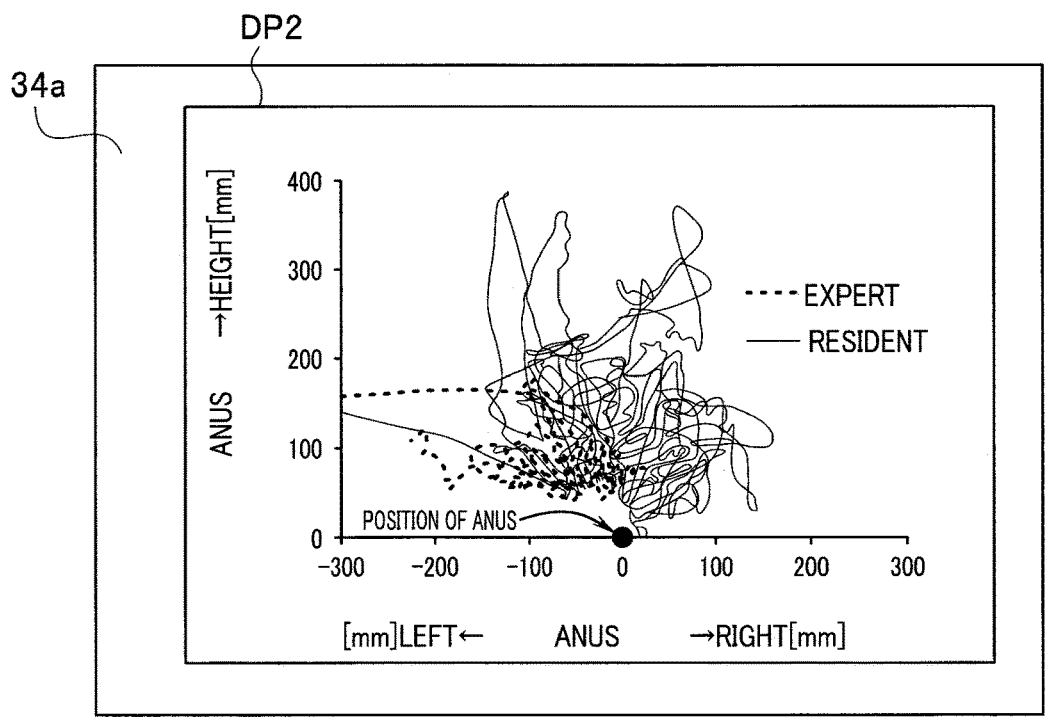
FIG. 14 is a diagram showing another example of the image showing the operation ranges of the right hands of the designated two doctors according to the embodiment of the present invention.

Like FIG. 13, FIG. 14 is a diagram showing another example of the image showing the operation ranges of the right hands RH of the designated two doctors. A screen shown in FIG. 14 is displayed according to a command different from the command shown in FIG. 13.

A window DP2 shown in FIG. 14 displays a graph showing changes of positions of the right hands RH at a time when the model 102 is viewed from the anus section 102c side. In FIG. 14 as well, it is seen that a movement of the right hand RH of the resident indicated by a solid line is more wasteful compared with a movement of the right hand RH of the expert indicated by a dotted line.

The respective graphs of FIG. 13 and FIG. 14 are drawn based on information of the position (x, y, z) of the movement of the hand in the table data TBL shown in FIG. 11.

Note that the graphs of FIG. 13 and FIG. 14 may be displayed to be gradually drawn according to elapse of time. For example, when the drawing is started from a point of a time point t0 and graph drawing is performed such that a line of the graph extends according to the elapse of time, it is easy to understand a movement of a hand of the user corresponding to the elapse of time. In other words, the endoscope insertion operation evaluation processor 33 may output display data for drawing, based on information of a position of the hand, the position of the hand as a graph according to the elapse of time.

Figure 15:
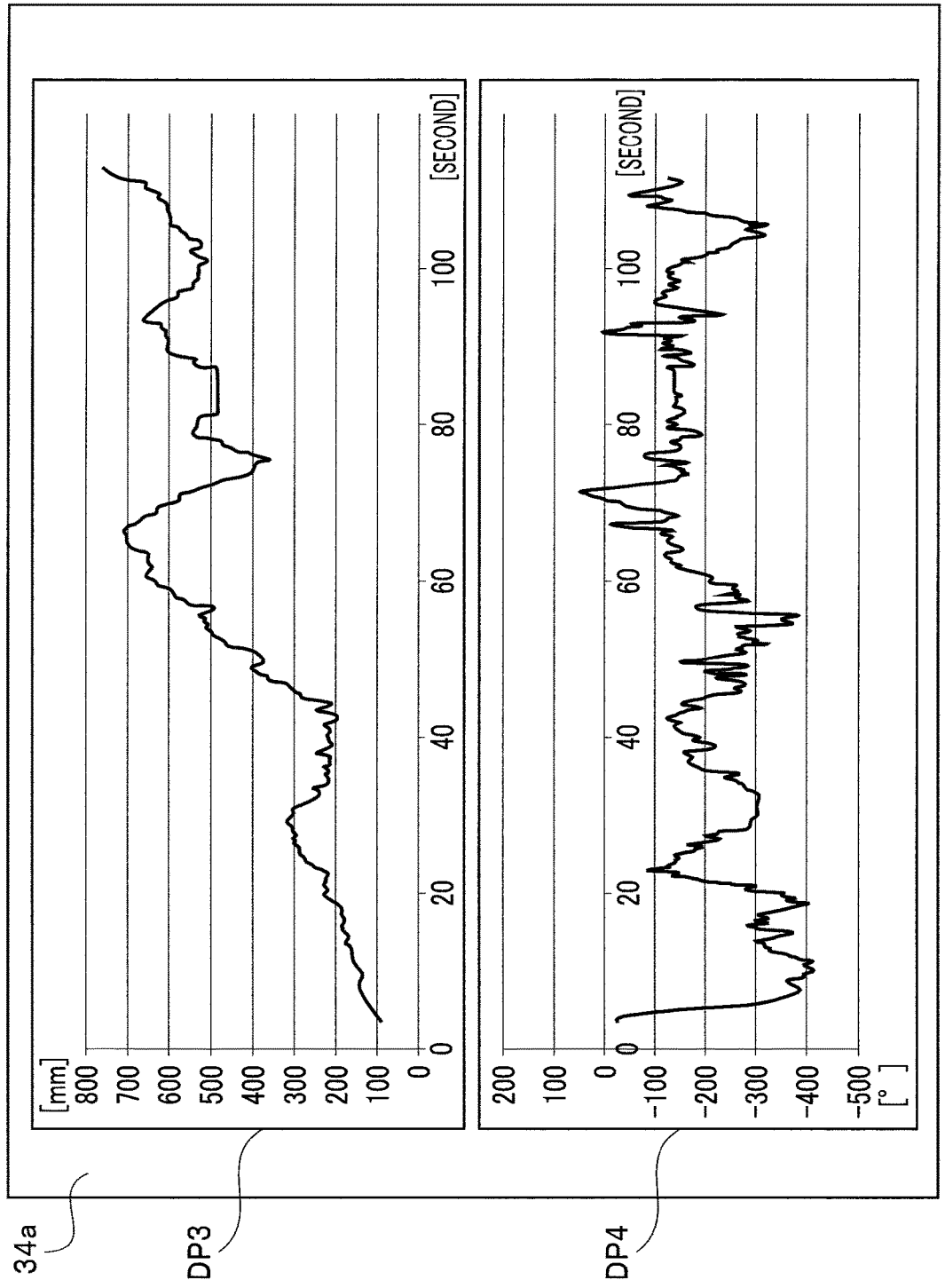
FIG. 15 is a diagram showing an example of an image showing a graph showing changes in an advance and retraction amount and a torsion amount of the insertion section according to the embodiment of the present invention.

2) An Advance and Retraction Amount and a Torsion Amount of the Insertion Section For example, the user sometimes desires to view a change in an advance and retraction amount (that is, push and pull) and a change in a torsion amount of the insertion section 6a at a time when the insertion section 6a is inserted into the large intestine. In that case, when the user inputs a predetermined command, windows DP3 and DP4 are displayed on the display screen 34a shown in FIG. 15. FIG. 15 is a diagram showing an example of an image showing a graph showing changes in an advance and retract amount and a torsion amount of the insertion section.

The window DP3 displays a graph showing the change in the advance and retraction amount (that is, push and pull) of the insertion section 6a. The window DP4 displays a graph showing an example of an image showing the change in the torsion amount of the insertion section 6a. When the user inputs the predetermined command, the image shown in FIG. 15 is displayed. In other words, the endoscope insertion operation evaluation processor 33 outputs first display data for displaying information concerning first parameters among a movement amount, moving speed, a turning angle, and turning speed of a hand within a first time period and second display data for displaying information concerning second parameters among the movement amount, the moving speed, the turning angle, and the turning speed of the hand within a second time period.

In FIG. 15, in the graph in the window DP3 and the graph in the window DP4, time axes of the horizontal axes are aligned, that is, synchronized. A period from approximately 20 seconds to 70 seconds is a time period when the distal end portion 11 of the insertion section 6a is passing through a sigmoid colon. A period from approximately 70 seconds to 90 seconds is a time period when the distal end portion 11 of the insertion section 6a is passing through a splenic flexure. A period from approximately 90 seconds to 100 seconds is a time period when the distal end portion 11 of the insertion section 6a is passing through a transverse colon. Accordingly, the user can learn, viewing these graphs, a push and pull amount of the insertion section 6a and a torsion amount of the insertion section 6a.

For example, in the case of FIG. 15, it is shown that the insertion section 6a is twisted while being pulled between 60 seconds and 80 seconds. Accordingly, when the user is the resident, if a push and pull amount of the insertion section 6a and a torsion amount of the insertion section 6a of the expert are displayed, it is possible to compares the push and pull amount of the expert with a push and pull amount and a torsion amount of the user and improve insertion operation of the user.

The respective graphs of FIG. 15 are drawn based on the information of the insertion amount (L) and the turning amount (R) of the insertion section 6a in the table data TBL in FIG. 11.

3) A Movement of the Hand and an Insertion Shape

Figure 16:
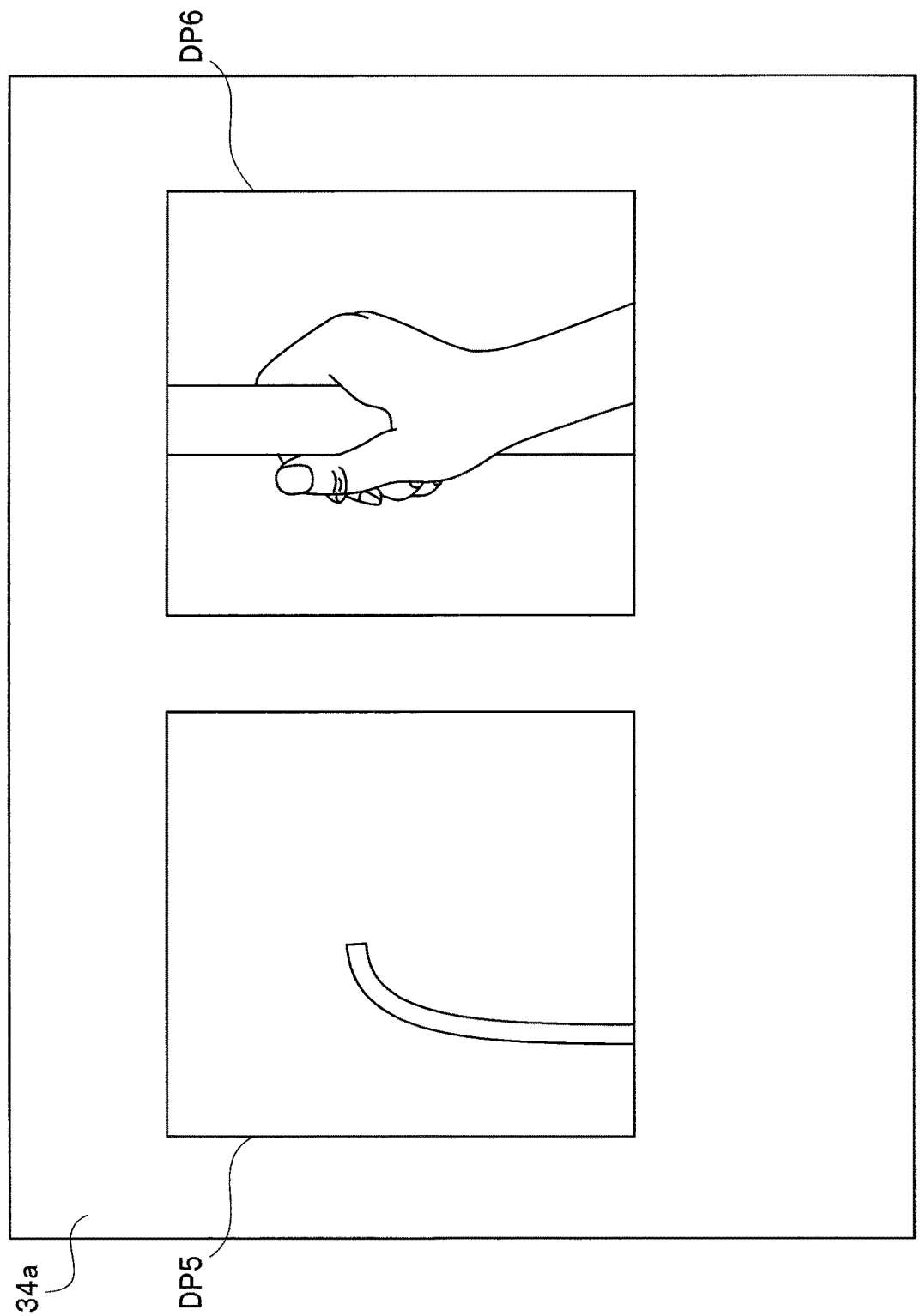
FIG. 16 is a diagram showing an example of an image showing a movement of a hand and a change of an insertion shape according to the embodiment of the present invention.

For example, the user sometimes desires to view how an insertion shape SR of the insertion section 6a changes according to a movement of the right hand RH. In that case, when the user inputs a predetermined command, windows DP5 and DP6 in the display screen 34a shown in FIG. 16 are displayed. FIG. 16 is a diagram showing an example of an image showing a movement of a hand and a change of an insertion shape.

The window DP5 displays the insertion shape IPF of the insertion section 6a. The window DP6 displays a movement of the right hand RH as an animation. When the user inputs a predetermined command, the image shown in FIG. 16 is displayed.

An insertion shape of the insertion section 6a is displayed in the window DP5. An animation image of the right hand is displayed in the window DP6. The animation generation program AP generates an animation image of a movement of the right hand RH from information of a position (x, y, z) and a posture (vx, vy, vz) of the right hand RH. In other words, the endoscope insertion operation evaluation processor 33 outputs display data for displaying, in synchronization with each other, an insertion shape and an animation image of a hand generated based on information of a position and a posture of the hand.

Figure 17:
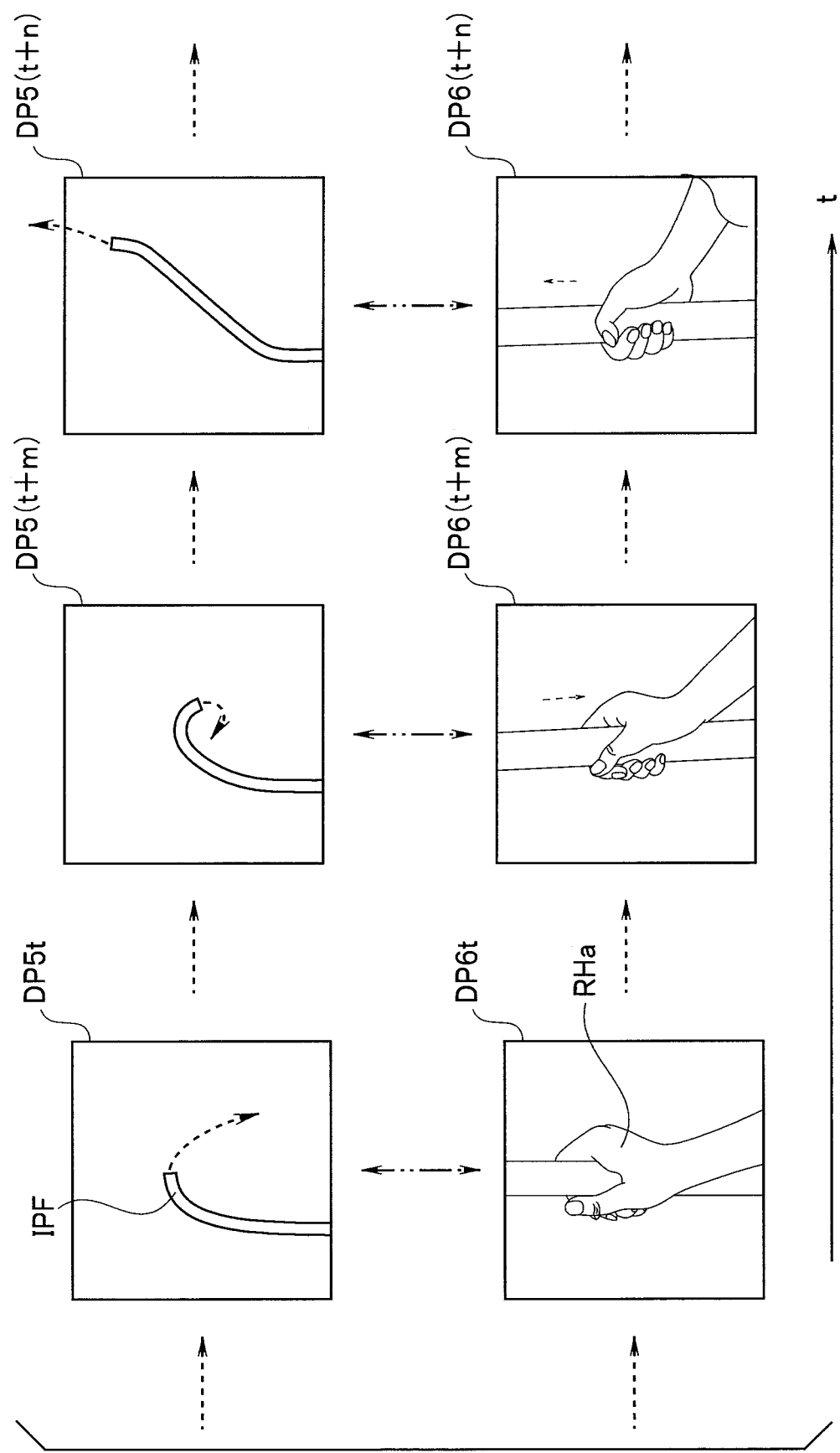
FIG. 17 is a diagram for explaining a change of an insertion shape and a change of a hand of an animation displayed in two windows according to the embodiment of the present invention.

FIG. 17 is a diagram for explaining a change of the insertion shape displayed in the window DP5 and a change of the hand of the animation displayed in the window DP6. FIG. 17 shows changes of images corresponding to elapse of time of the two windows DP5 and DP6. Windows DP5t and DP6*t* show images at the same time point t, windows DP5(*t*+m) and DP6(*t*+m) show images at the same time point (t+m) elapsed from the time point t, and windows DP5(*t*+n) and DP6(*t*+n) show images at the same time point (t+n) elapsed from the time point (t+m).

As shown in FIG. 17, the insertion shape IPF of the insertion section 6*a* and a right hand RHa of an animation are displayed in the two windows DP5 and DP6 shown in FIG. 16 in synchronization with each other. Accordingly, the user can learn how the insertion shape IPF of the insertion section 6*a* change according to a movement of the right hand RH.

Unlike a rigid instrument, in a flexible endoscope such as a large intestine endoscope, the insertion section 6*a* of the endoscope 6 does not always operate in a one-to-one relation with operation of a doctor. For example, when the doctor pushes the endoscope 6 into a subject, in some case, the endoscope 6 bends in an intestinal tract and the distal end portion 11 of the endoscope 6 does not proceed to depth of the intestinal tract. In such a case, in general, a resident often cannot recognize how the insertion section 6*a* inserted into a body moves in response to endoscope operation of the resident. Therefore, for the resident, it is extremely important in learning insertion operation to know how the insertion shape IPF of the insertion section 6*a* changes in response to a movement of the right hand RH.

An image in the window DP5 shown in FIG. 16 is drawn based on shape information in the table data TBL in FIG. 11. An image in the window DP6 shown in FIG. 16 is created and drawn by the animation generation program AP based on the information of the position, the posture, and the torsion amount during the movement of the hand in the table data TBL shown in FIG. 11. In particular, since the movement of the hand is displayed as an amination and the insertion shape of the insertion section is displayed in synchronization, it is easy to understand the movement of the hand and the insertion shape of the insertion section.

Note that in FIG. 16, only the insertion shape IPF is displayed in the window DP5. However, an image obtained by superimposing the insertion shape IPF on an image of the model 102 picked up by the bird's eye view camera 36 may be displayed.

Figure 18:
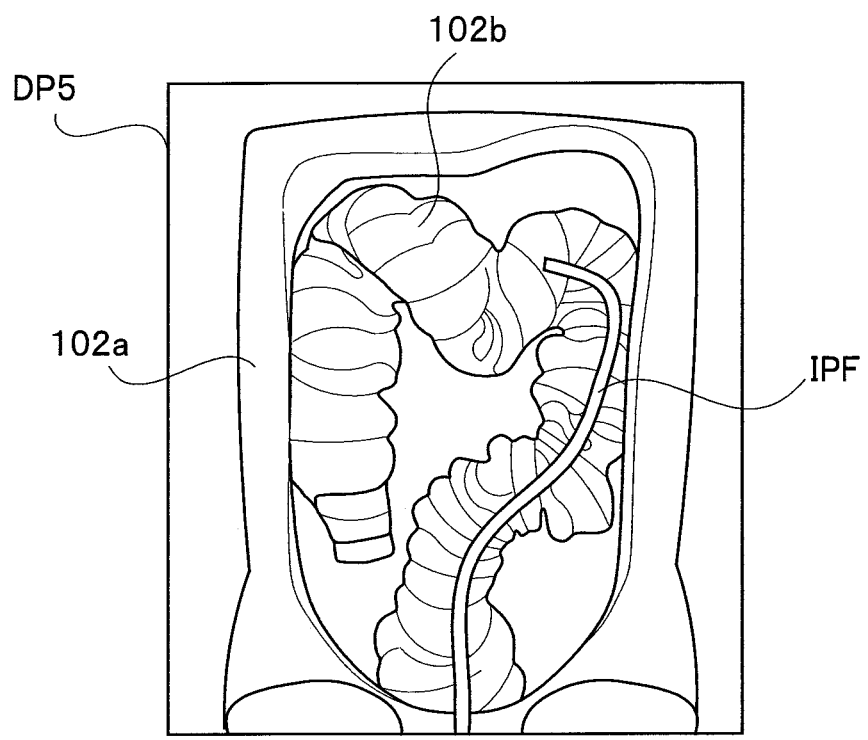
FIG. 18 is a diagram showing an example of an image obtained by superimposing an insertion shape on an image of the model, the image being displayed in a window, according to the embodiment of the present invention.

FIG. 18 is a diagram showing an example of the image obtained by superimposing the insertion shape IPF on the image of the model 102, the image being displayed in the window DP5. With the image shown in FIG. 18, the user can easily understand a state of the insertion section 6*a* in the intestinal tract section 102*b*.

Note that if the table data TBL explained above is used, various kinds of display can be performed other than the display examples explained above.

The endoscope insertion operation evaluation processor 33 may acquire various kinds of information from the endoscope apparatus 2 and generate and output display data including information concerning operation on the endoscope apparatus 2 by the user. For example, when hardness variable operation for the insertion section 6*a* is performed, if display data including information indicating that the hardness variable operation is performed is generated, the user can evaluate the insertion operation and the information concerning the operation on the endoscope apparatus 2 in correlation with each other.

Furthermore, a position of the distal end portion 11 of the insertion section 6*a* may be estimated from shape information of the endoscope shape acquisition apparatus 3. Display data including information concerning the estimated position may be generated and outputted. Based on the position information of the distal end portion 11, a message such as "passing through the sigmoid colon" can also be displayed on a graph displayed on the display apparatus 34.

Figure 19:
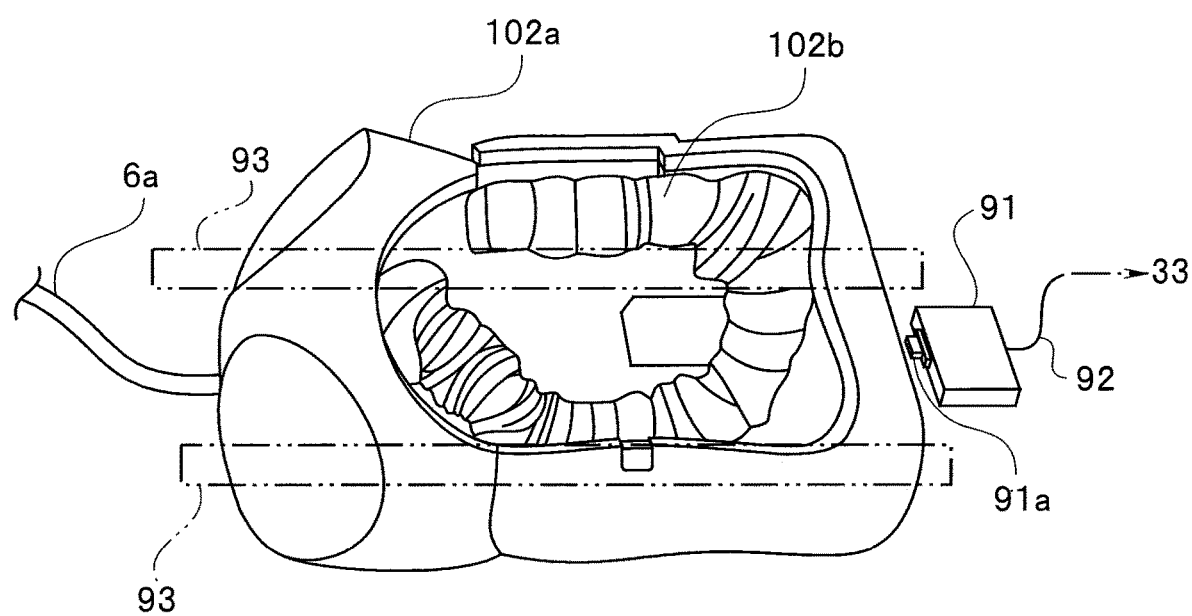
FIG. 19 is a diagram for explaining disposition of a force gauge functioning as an amount of force sensor according to the embodiment of the present invention.

Note that an amount of force sensor that can detect an amount of force by operation of the user may be provided in the model 102. FIG. 19 is a diagram for explaining disposition of a force gauge functioning as the amount of force sensor. A force gauge 91 measures pushing and pulling force. The force gauge 91 is provided on the table 101 such that a sensor unit 91*a* for amount of force detection of the force gauge 91 comes into contact with a surface of the model 102 on an opposite side of the anus section 102*c*. A cable 92 for outputting a measurement signal extends from the force gauge 91.

The model 102 is fixed on two linear guide rails 93 fixed on the table 101. In other words, the model 102 functioning as a subject is mounted on the two linear guide rails 93, which are mounts that smoothly move in a predetermined range in a longitudinal direction in a direction in which the insertion section 6*a* is inserted. The model 102 is fixed on the linear guide rails 93 to move within the predetermined range on the linear guide rails 93. The force gauge 91 is fixed to the table 101 such that the sensor unit 91*a* of the force gauge 91 comes into contact with the model 102. Note that the linear guide rails 93 may be one linear guide rail. The model 102 can be moved in the longitudinal direction by a method of, for example, rolling the model 102 with a roller or magnetically levitating the model 102.

As shown in FIG. 19, an output of the force gauge 91 is outputted to the endoscope insertion operation evaluation processor 33 by the cable 92. The endoscope insertion operation evaluation processor 33 receives a measurement signal of the force gauge 91. Accordingly, the force gauge 91 configures an amount-of-force detecting unit that detects force applied to the model 102, which is the subject, or the insertion section 6*a*.

It is possible to detect an amount of force, that is, push and pull force by operation of the insertion section 6*a* by the user using the force gauge 91 provided in this way. In other words, the force gauge 91 detects force applied to the subject or the insertion section 6*a* in the longitudinal direction in the direction in which the insertion section 6*a* is inserted and a direction different from the longitudinal direction (an opposite direction). Note that the force gauge 91 may detect only force in one of the longitudinal direction in the direction in which the insertion section 6*a* is inserted and the direction different from the longitudinal direction (the opposite direction).

Figure 20:
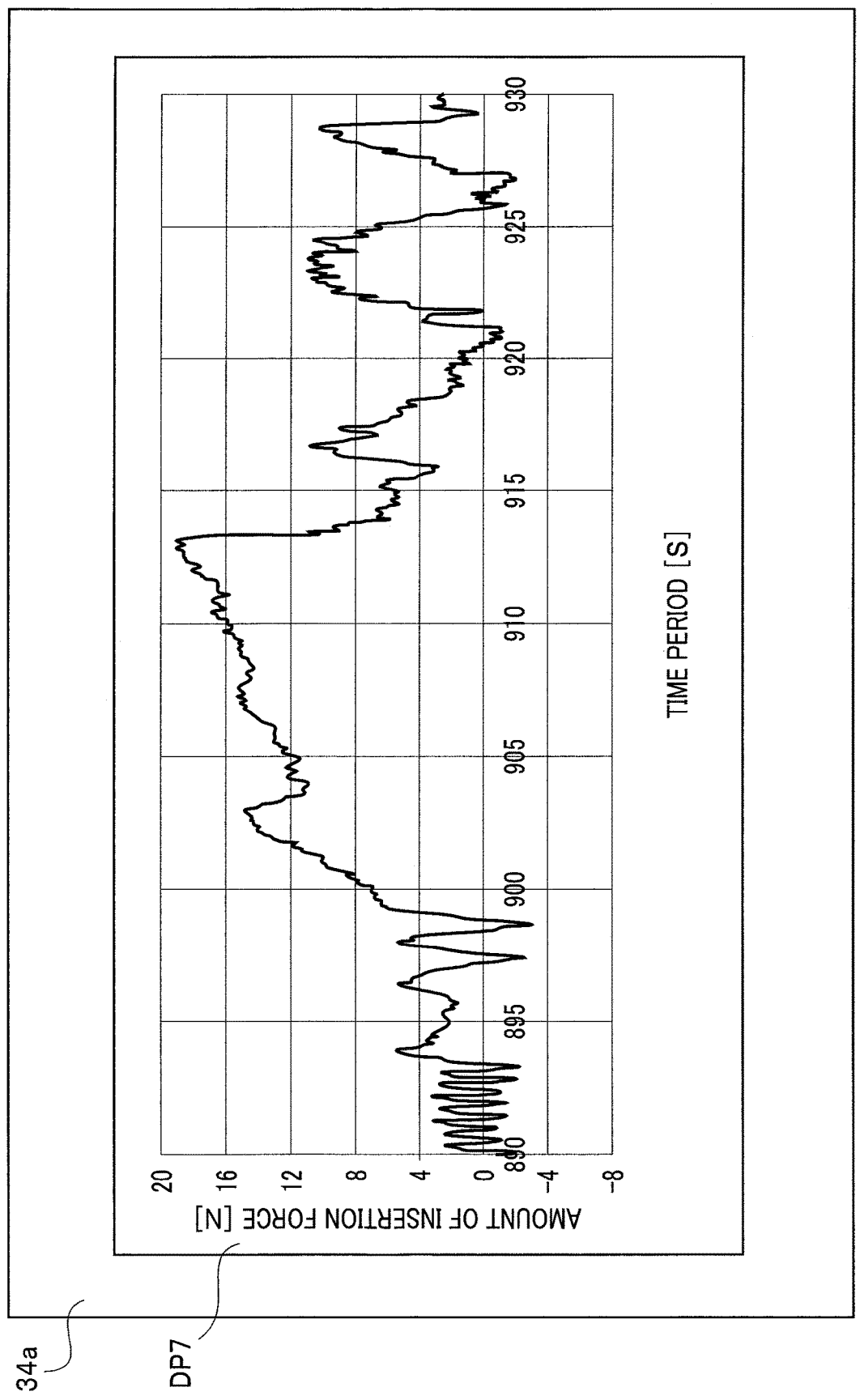
FIG. 20 is a diagram showing an example of an image showing a graph showing a change in an amount of force applied to the model according to the embodiment of the present invention.

FIG. 20 is a diagram showing an example of an image showing a graph showing a change in an amount of force applied to the model. The endoscope insertion operation evaluation processor 33 outputs information concerning the force temporally in correlation with information concerning the insertion shape IPF. As a result, a graph of a change in an amount of insertion force corresponding to elapse of time is displayed in a window DP7. If the graph shown in FIG. 20 is arranged in a pair as shown in FIG. 15, the user can easily learn a difference between amounts of insertion force of two doctors.

As explained above, with the embodiment explained above, it is possible to provide a monitoring system and an evaluation method for insertion operation of an endoscope that can present an endoscope insertion operation method that can present how a hand gripping an insertion section should be moved.

Note that as a sensor that can detect an amount of force for inserting the insertion section 6*a* into the model 102 with operation of the user, for example, a not-shown torque sensor that measures turning force on a hand side of the user (at which torque the user is twisting the insertion section 6a) may be further added other than the force gauge 91 and information from the torque sensor may be added to a detection result.

Since the user can display desired display data using data for evaluation, the user can perform evaluation of insertion operation. In particular, since the movement information of the hand and the insertion shape information of the endoscope shape acquisition apparatus 3 are recorded temporally in correlation with each other, the user can check the movement of the hand and the insertion shape of the insertion section 6a in correlation with each other.

Note that the embodiment explained above is explained as the endoscope insertion training system for training in the insertion operation of the endoscope. However, the embodiment is also applicable to a system not for training but for simply evaluating the insertion operation.

As example of the embodiment explained above is the insertion operation of the endoscope into the model. However, the embodiment can also be used as an evaluation apparatus for insertion operation into a patient or the like.

Furthermore, in the present embodiment, a recording function, a display function, and the like of the endoscope insertion operation evaluation processor 33 are executed by software. However, the respective functions may be configured as individual electronic circuits or may be configured as circuit blocks in an integrated circuit such as an FPGA (field programmable gate array). In the present embodiment, for example, the endoscope insertion operation evaluation processor 33 may include one or more CPUs.

The present invention is not limited to the embodiment explained above. Various changes, alterations, and the like are possible within a range not changing the gist of the invention.

What is claimed is:

1. A monitoring system comprising:
    a shape detection apparatus configured to detect an insertion shape of an insertion section of an endoscope inserted into a subject;
    a movement detection apparatus configured to detect a movement including at least one of a position or a posture, in a three-dimensional space, of a hand with which an operator operating the endoscope grips the insertion section; and
    a processor configured to calculate, based on information outputted from the movement detection apparatus, at least one parameter of a movement amount, moving speed, a turning angle, or turning speed of the hand and output, temporally in correlation with each other, the at least one parameter and information outputted from the shape detection apparatus of a corresponding insertion shape of the insertion section;
    wherein the movement detection apparatus is a motion capture apparatus including a first image pickup apparatus configured to pick up an image of a marker apparatus attached to the hand of the operator, the motion capture apparatus detecting a movement of the hand from a movement of the marker apparatus, the image of which is picked up by the first image pickup apparatus.

2. The monitoring system according to claim 1, wherein the marker apparatus includes a plurality of markers and is configured to be attached to a wrist of the hand of the operator, and
    the first image pickup apparatus includes a plurality of cameras configured to pick up images of the plurality of markers in a plurality of directions in the three-dimensional space.

3. The monitoring system according to claim 2, wherein at least two markers among the plurality of markers are disposed to be separated by 80 mm or more to make it possible to detect, with any one of the plurality of cameras, the plurality of markers projecting from the wrist.

4. The monitoring system according to claim 1, further comprising a second image pickup apparatus configured to pick up an image of the insertion section inserted into the subject, wherein
    the processor calculates, based on a picked-up image of the second image pickup apparatus, a predetermined parameter based on a predetermined indicator provided on an outer surface of the insertion section, the image of which is picked up by the second image pickup apparatus, and outputs the predetermined parameter temporally in correlation with the information of the insertion shape of the insertion section.

5. The monitoring system according to claim 4, wherein the predetermined indicator includes a first band annularly surrounding an outer circumference of the insertion section in a direction orthogonal to a longitudinal axis of the insertion section and a second band provided to be tilted with respect to the first band and spirally surrounding the outer circumference of the insertion section.

6. The monitoring system according to claim 1, wherein the processor outputs display data for displaying, in synchronization with each other, the insertion shape and an animation image of the hand generated based on information of the position and the posture.

7. The monitoring system according to claim 1, wherein the processor outputs, based on information of the position in the three-dimensional space of the hand, display data for drawing the position of the hand in a graph at predetermined intervals of time.

8. A monitoring system comprising:
    a shape detection apparatus configured to detect an insertion shape of an insertion section of an endoscope inserted into a subject;
    a movement detection apparatus configured to detect a movement including at least one of a position or a posture, in a three-dimensional space, of a hand with which an operator operating the endoscope grips the insertion section;
    a processor configured to calculate, based on information outputted from the movement detection apparatus, at least one parameter of a movement amount, moving speed, a turning angle, or turning speed of the hand and output, temporally in correlation with each other, the at least one parameter and information outputted from the shape detection apparatus of a corresponding insertion shape of the insertion section; and
    a force gauge configured to detect force applied to the subject or the insertion section,
    wherein the processor outputs information of the force temporally in correlation with the information of the insertion shape.

9. The monitoring system according to claim 8, wherein the subject is mounted on a mount that moves in a predetermined range in a longitudinal direction in a direction in which the insertion section is inserted, and the force gauge detects force applied to the subject or the insertion section in at least one of the longitudinal direction or a direction different from the longitudinal direction.

10. A monitoring system comprising:
a shape detection apparatus configured to detect an insertion shape of an insertion section of an endoscope inserted into a subject;
a movement detection apparatus configured to detect a movement including at least one of a position or a posture, in a three-dimensional space, of a hand with which an operator operating the endoscope grips the insertion section; and
a processor configured to calculate, based on information outputted from the movement detection apparatus, at least one parameter of a movement amount, moving speed, a turning angle, or turning speed of the hand and output, temporally in correlation with each other, the at least one parameter and information outputted from the shape detection apparatus of a corresponding insertion shape of the insertion section;
wherein the processor outputs first display data for displaying information of a first parameter among the movement amount, the moving speed, the turning angle, and the turning speed of the hand within a first time period and second display data for displaying information of a second parameter among the movement amount, the moving speed, the turning angle, and the turning speed of the hand within a second time period.

* * * * *